US012465778B2

(12) United States Patent
Paradis

(10) Patent No.: US 12,465,778 B2
(45) Date of Patent: Nov. 11, 2025

(54) MULTIMODAL DEVICE AND METHOD TO INCREASE THE EFFICACY OF TRANSTHORACIC CARDIOVERSION OR CARDIAC PACING IN PATIENTS WITH PERFUSING RHYTHMS

(71) Applicant: Norman Alan Paradis, Putney, VT (US)

(72) Inventor: Norman Alan Paradis, Putney, VT (US)

( * ) Notice: Subject to any disclaimer, the term of this patent is extended or adjusted under 35 U.S.C. 154(b) by 545 days.

(21) Appl. No.: 17/942,041

(22) Filed: Sep. 9, 2022

(65) Prior Publication Data

US 2023/0001220 A1 Jan. 5, 2023

Related U.S. Application Data

(63) Continuation-in-part of application No. 17/676,612, filed on Feb. 21, 2022, now Pat. No. 12,285,621, (Continued)

(51) Int. Cl.
*A61N 1/00* (2006.01)
*A61H 31/00* (2006.01)
*A61N 1/39* (2006.01)

(52) U.S. Cl.
CPC ....... *A61N 1/39044* (2017.08); *A61H 31/005* (2013.01)

(58) Field of Classification Search
CPC .............. A61N 1/39044; A61N 1/3601; A61N 1/36014; A61H 31/005; A61H 2201/10; (Continued)

(56) References Cited

U.S. PATENT DOCUMENTS 2,699,163 A 1/1955 Engstrom
2,899,955 A 8/1959 Huxley, III et al.
(Continued)

FOREIGN PATENT DOCUMENTS

EP 2709581 B1 7/2017
EP 3431069 A1 1/2019
(Continued)

OTHER PUBLICATIONS

Plaisance, M.D., Patrick, A Comparison of Standard Cardiopulmonary Resuscitation and Active Compression- Decompression Resuscitation for Out-of-Hospital Cardiac Arrest, New England Journal of Medicine, vol. 341, No. 8, Aug. 19, 1999, pp. 569-575.
(Continued)

*Primary Examiner* — Scott M. Getzow
(74) *Attorney, Agent, or Firm* — Nathaniel A. Wickliffe; Patent Attorney

(57) ABSTRACT

The invention disclosed here relates in general to the field of medical devices. In particular, to devices and methods for improving the clinical outcome of patients suffering from cardiac dysrhythmias without cardiac arrest. This method and/or device integrates mechanical, pneumatic, acoustic and/or electrophysiologic capabilities with electrical countershock or pacing capabilities such that the probability of successful cardioversion or pacing is increased. The sequence, forces, and electrical properties of the subsystems can be computer controlled and adjusted in response to biomarker inputs.

20 Claims, 9 Drawing Sheets

Related U.S. Application Data which is a continuation of application No. 16/514,968, filed on Jul. 17, 2019, now Pat. No. 11,253,713.

(60) Provisional application No. 62/699,647, filed on Jul. 17, 2018.

(58) Field of Classification Search
CPC .... A61H 2201/1621; A61H 2201/5007; A61H 31/006; A61H 2205/084; A61H 23/02; A61H 2230/655
See application file for complete search history.

(56) References Cited

U.S. PATENT DOCUMENTS

| | | | |
|---|---|---|---|
| 3,364,924 A | 1/1968 | Barkalow | |
| 3,481,327 A | 12/1969 | Drennen | |
| 3,683,655 A | 8/1972 | White et al. | |
| 4,198,963 A | 4/1980 | Barkalow et al. | |
| 4,349,015 A | 9/1982 | Alferness | |
| 4,397,306 A | 8/1983 | Weisfeldt et al. | |
| 4,424,806 A | 1/1984 | Newman et al. | |
| 4,664,098 A | 5/1987 | Woudenberg et al. | |
| 4,770,164 A | 9/1988 | Lach et al. | |
| 4,838,263 A | 6/1989 | Warwick et al. | |
| 4,840,167 A | 6/1989 | Olsson et al. | |
| 4,928,674 A | 5/1990 | Halperin et al. | |
| 5,076,259 A | 12/1991 | Hayek | |
| 5,078,134 A * | 1/1992 | Heilman | A61N 1/046 607/142 |
| 5,222,478 A | 6/1993 | Scarberry et al. | |
| 5,454,779 A | 10/1995 | Lurie et al. | |
| 5,490,820 A | 2/1996 | Schock et al. | |
| 5,496,257 A | 3/1996 | Kelly | |
| 5,743,864 A | 4/1998 | Baldwin, Ii | |
| 5,769,800 A | 6/1998 | Gelfand et al. | |
| 6,171,267 B1 | 1/2001 | Baldwin, Ii | |
| 6,174,295 B1 | 1/2001 | Cantrell et al. | |
| 6,213,960 B1 | 4/2001 | Sherman et al. | |
| 6,224,562 B1 | 5/2001 | Lurie et al. | |
| 6,374,827 B1 | 4/2002 | Bowden et al. | |
| 6,390,996 B1 | 5/2002 | Halperin et al. | |
| 6,393,316 B1 | 5/2002 | Gillberg et al. | |
| 6,418,342 B1 | 7/2002 | Owen et al. | |
| 6,427,685 B1 | 8/2002 | Ray | |
| 6,752,771 B2 | 6/2004 | Rothman et al. | |
| 6,827,695 B2 | 12/2004 | Palazzolo et al. | |
| 6,869,409 B2 | 3/2005 | Rothman et al. | |
| 7,032,596 B2 | 4/2006 | Thompson et al. | |
| 7,220,235 B2 | 5/2007 | Geheb et al. | |
| 8,433,412 B1 | 4/2013 | Westlund et al. | |
| 8,478,401 B2 | 7/2013 | Freeman | |
| 8,795,208 B2 | 8/2014 | Walker | |
| 9,474,892 B2 | 10/2016 | Chang et al. | |
| 10,245,209 B2 | 4/2019 | Lurie et al. | |
| 10,772,793 B2 | 9/2020 | Paradis | |
| 10,888,493 B2 | 1/2021 | Freeman et al. | |
| 10,918,354 B2 | 2/2021 | Nichol et al. | |
| 11,097,118 B2 | 8/2021 | Freeman et al. | |
| 11,679,059 B2 | 6/2023 | Paradis | |
| 11,684,541 B2 | 6/2023 | Paradis | |
| 11,684,542 B2 | 6/2023 | Paradis | |
| 11,744,772 B2 | 9/2023 | Fabian et al. | |
| 2001/0007928 A1 | 7/2001 | Hansen | |
| 2002/0026131 A1 | 2/2002 | Halperin | |
| 2003/0004445 A1 | 1/2003 | Hall et al. | |
| 2004/0162510 A1 * | 8/2004 | Jayne | A61H 31/005 601/44 |
| 2004/0230140 A1 | 11/2004 | Steen | |
| 2006/0089574 A1 | 4/2006 | Paradis | |
| 2007/0010765 A1 | 1/2007 | Rothman et al. | |
| 2007/0032829 A1 | 2/2007 | Ostroff | |
| 2007/0060785 A1 | 3/2007 | Freeman et al. | |
| 2007/0225623 A1 | 9/2007 | Freeman | |
| 2007/0299473 A1 * | 12/2007 | Matos | A61N 1/3904 607/9 |
| 2008/0097534 A1 | 4/2008 | Myklebust et al. | |
| 2008/0275371 A1 | 11/2008 | Hoffmann | |
| 2009/0062701 A1 | 3/2009 | Yannopoulos et al. | |
| 2010/0004572 A1 | 1/2010 | King | |
| 2012/0016179 A1 | 1/2012 | Paradis et al. | |
| 2012/0116272 A1 | 5/2012 | Hampton et al. | |
| 2012/0146797 A1 | 6/2012 | Oskin et al. | |
| 2014/0094724 A1 | 4/2014 | Freeman | |
| 2014/0155792 A1 | 6/2014 | Karve et al. | |
| 2014/0213942 A1 | 7/2014 | Hanson | |
| 2014/0336546 A1 | 11/2014 | Chapman et al. | |
| 2014/0358047 A1 | 12/2014 | Lurie | |
| 2015/0094624 A1 | 4/2015 | Illindala | |
| 2015/0265497 A1 | 9/2015 | Kaufman et al. | |
| 2016/0317385 A1 | 11/2016 | Salcido et al. | |
| 2016/0361228 A1 | 12/2016 | Paradis et al. | |
| 2017/0035650 A1 | 2/2017 | Taylor et al. | |
| 2017/0105898 A1 | 4/2017 | Taylor et al. | |
| 2017/0266078 A1 | 9/2017 | Jayne et al. | |
| 2018/0021216 A1 | 1/2018 | Paradis et al. | |
| 2018/0168922 A1 | 6/2018 | Chapman et al. | |
| 2019/0091099 A1 | 3/2019 | Nilsson et al. | |
| 2019/0117501 A1 | 4/2019 | Chapman et al. | |
| 2019/0209428 A1 | 7/2019 | Paradis | |

FOREIGN PATENT DOCUMENTS

| | | |
|---|---|---|
| EP | 3977974 A1 | 4/2022 |
| JP | 2022048134 A | 3/2022 |
| KR | 101383051 B | 4/2014 |
| KR | 20160146462 A | 12/2016 |
| WO | 9628128 A1 | 9/1996 |
| WO | 9965560 A2 | 12/1999 |
| WO | 2010099628 A1 | 9/2010 |
| WO | 2014051934 A1 | 4/2014 |
| WO | 2015048347 A1 | 4/2015 |

OTHER PUBLICATIONS

Plaisance, P., et al. "Use of an inspiratory impedance threshold device on a facemask and endotracheal tube to reduce intrathoracic pressures during the decompression phase of active compression-decompression cardiopulmonary resuscitation." Crit Care Med. 33.5 (2005): 990-94.

Qvigstad et al., "Clinical pilot study of different hand positions during manual chest compressions monitored with capnography", Resuscitation 84 (2013) 1203-1207, www.elsevier.com/locate/resuscitation.

Ralston, Sandra H., Cardiopulmonary Resuscitation with Interposed Abdominal Compression in Dogs, Anesthesia and Analgesia, vol. 61, No. 8, Aug. 1982, pp. 645-651.

Ramirez et al., "Effect of Applying Force to Self-Adhesive Electrodes on Transthoracic Impedance: Implications for Electrical Cardioversion", PACE, vol. 39, Oct. 2016, pp. 1141-1147.

Rubertsson S, Lindgren E, Smekal D et al. "Mechanical chest compressions and simultaneous defibrillation vs conventional cardiopulmonary resuscitation in out-of-hospital cardiac arrest: the LINC randomized trial". JAMA 2014; 311(1):53-61.

Rudikoff, M. T., et al. "Mechanisms of Blood Flow During Cardiopulmonary Resuscitation." Circulation 61 (1980): 345-52.

Sanders AB, Kern KB, Ewy GA, Atlas M, Bailey L. "Improved resuscitation from cardiac arrest with open-chest massage". Ann Emerg Med 1984; 13(9 Pt 1):672-675.

Sanders, A.B., K.B. Kern, C.W. Otto, M.M. Milander, and G.A. Ewy. 1989. 'End-tidal carbon dioxide monitoring during cardiopulmonary resuscitation. A prognostic indicator for survival.', JAMA, 262: 1347-51.

Segal, M.D., PhD, Nicolas, Intermittent Positive-Pressure Ventilation, Chest Compression Synchronized Ventilation, Bilevel Ventilation, Continuous Chest Compression, Active Compression Decompression, and Impedance Threshold Device-The Complexity of Ventilation During Cardiopulmonary Resuscitation, Critical Care Medicine, Feb. 2014, vol. 42, No. 2, pp. 480-481.

(56) References Cited

OTHER PUBLICATIONS

Shinar Z, Bellezzo J, Paradis N. et al. "Emergency department initiation of cardiopulmonary bypass: a case report and review of the literature". J Emerg Med 2012; 43(1):83-86.
Stephenson HE, Corsan Reed L, Hinton JW. "Some Common Denominators in 1200 cases of cardiac arrest". Ann Surg 1953; 137:731-744.
Stiell IG, Nichol G, Leroux BG et al. "Early versus later rhythm analysis in patients with out-of-hospital cardiac arrest". N Engl J Med 2011; 365(9):787-797.
Vector Definition; 2020; Merriam-Webster; https://www.merriam-webster.com/dictionary/vector (Year: 2020).
Voorhees, PhD, William D et al., Improved Oxygen Delivery During Cardiopulmonary Resuscitation with Interposed Abdominal Compressions, Annals of Emergency Medicine, 12:Mar. 3, 1983, pp. 128-135.
Wang, M.D., Chih-Hung, et al., Active Compression-Decompression Resuscitation and Impedance Threshold Device for Out-of-Hospital Cardiac Arrest: A Systematic Review and Metaanalysis of Randomized Controlled Trials, Critical Sare Medicine, Apr. 2015, vol. 43, No. 4, pp. 889-896.
Weisfeldt, M.D., M.L., et al., Increased intrathoracic pressure—no direct heart compression—causes the rise in intrathoracic vascular pressures during CPR in dogs and pigs, Critical Care Medicine, pp. 377-378, May 1981.
Wik L, Olsen JA, Persse D et al. "Manual vs. integrated automatic load-distributing band CPR with equal survival after out of hospital cardiac arrest. The randomized CIRC trial". Resuscitation 2014; 85(6):741-748.
Wolcke, Md., Benno G., et al., Comparison of Standard Cardiopulmonary Resuscitation Versus the Combination of Active Compression-Decompression Cardiopulmonary Resuscitation and an Inspiratory Impedance Threshold Device for Out-of-Hospital Cardiac Arrest, Circulation, 2003, pp. 108, 2201-2205.
Xie, Z., Q. Yang, M. Li, Z. Huang, Y. Wang, Q. Ling, W. Tang, and Z. Yang. 2018. 'Amplitude screening improves performance of AMSA method for predicting success of defibrillation in swine model', Am J Emerg Med.
Yang, Z., et al. A tourniquet assisted cardiopulmonary resuscitation augments myocardial perfusion in a porcine model of cardiac arrest, Resuscitation 86 (2015) 49-53.
Yeung, J., et al., The use of CPR feedback/prompt devices during training and CPR performance: A systematic review, Resuscitation, 80, pp. 743-751, 2009.
Zoll, P. M., A. J. Linenthal, W. Gibson, M. H. Paul, and L. R. Norman. 1956. 'Termination of ventricular fibrillation in man by externally applied electric countershock', N Engl J Med, 254: 727-32.
Abella, Benjamin S. et al., CPR quality improvement during in-hospital cardiac arrest using a real-time audiovisual feedback system, Resuscitation, 2007, 73, pp. 54-61.
Aiello et al., "Real-time ventricular fibrillation amplitude-spectral area analysis to guide timing of shock delivery improves defibrillation efficacy during cardiopulmonary resuscitation in swine", Journal of the American Heart Association, DOI: 10.1161/JAHA.117.006749, pp. 1-15.
Arntz, H.R., et al. Phased Chest and Abdominal Compression-Decompression Versus Conventional Cardiopulmonary Resuscitation in Out-of-Hospital Cardiac Arrest, American Heart Association, Inc., Aug. 14, 2001, pp. 768-772.
Aufderheide, T. P., et al. "Clinical evaluation of an inspiratory impedance threshold device during standard cardiopulmonary resuscitation in patients with out-of-hospital cardiac arrest." Crit Care Med. 33.4 (2005): 734-40.
Babbs, MD, Charles F., Preclinical Studies of Abdominal Counterpulsation in CPR, Annals of Emergency Medicine, 13: Sep. 9, 1984, pp. 761-763.
Barkalow, B. H. "Comparison of miniaturized pneumatic chest compressor to Thumper." Resuscitation 79.3 (2008): 509.
Beck, C. S., E. C. Weckesser, and F. M. Barry. 1956. 'Fatal heart attack and successful defibrillation; new concepts in coronary artery disease', J Am Med Assoc, 161: 434-6.
Berkowitz, Ivor D., et al., Blood Flow during Cardiopulmonary Resuscitation with Simultaneous Compression and Ventilation in Infant Pigs, Pediatric Research, 1989, vol. 26, No. 6, pp. 558-564.
Bircher, N., et al, Do Intrathoracic Pressure Fluctuation or Heart Compressions Move Blood During External Cardiopulmonary Resuscitation (CPR)?, Resuscitation Research Center and the Department of Anesthesiology, University of Pittsburgh, ASA Abstract, V53, No. 3, Sep. 1980.
Cabanas, J. G., J. B. Myers, J. G. Williams, V. J. De Maio, and M. W. Bachman. 2015. 'Double Sequential External Defibrillation in Out-of-Hospital Refractory Ventricular Fibrillation: A Report of Ten Cases', Prehosp Emerg Care, 19: 126-30.
Callaway, Clifton W.; Why We Should No. Longer Terminate Resuscitations after 20 Minutes; Mar. 2, 2016; Journal of Emergency Medical Services; vol. 41, Issue 3; (Year: 2016).
Cave DM, Gazmuri RJ, Otto CW et al. "Part 7: CPR techniques and devices: 2010 American Heart Association Guidelines for Cardiopulmonary Resuscitation and Emergency Cardiovascular Care". Circ 2010; 122(18 Suppl 3): S720-S728.
Chan PS, McNally B, Tang F, Kellermann A. "Recent trends in survival from out-of-hospital cardiac arrest in the United States" Circ 2014; 130(21):1876-1882.
Cohen, Todd J., et al., Active Compression-Decompression Resuscitation: A Novel Method of Cardiopulmonary Resuscitation, American Heart Journal, Nov. 1992, pp. 1145-1150.
Cohen, Todd J., et al., Active Compression-Decompression, A New Method of Cardiopulmonary Resuscitation, JAMA, Jun. 3, 1992, vol. 267, No. 21, pp. 2916-2923.
Deakin, C. D., R. M. McLaren, G. W. Petley, F. Clewlow, and M. J. Dalrymple-Hay. 1998. 'Effects of positive end- expiratory pressure on transthoracic impedance—implications for defibrillation', Resuscitation, 37: 9-12.
Esibov A, Banville I, Chapman FW, Boomars R, Box M, Rubertsson S. "Mechanical chest compressions improved aspects of CPR in the LINC trial". Resuscitation 2015; 91:116-121.
Ewy, G.A., D.A. Hellman, S. McClung, and D. Taren. 1980. 'Influence of ventilation phase on transthoracic impedance and defibrillation effectiveness', Crit. Care Med, 8: 164-66.
Haas, Thorsten, et al., Revisiting the cardiac versus thoracic pump mechanism during cardiopulmonary resuscitation, Resuscitation, 58, Nov. 5, 2002, pp. 113-116.
Hallstrom A, Rea TD, Sayre MR et al. "Manual chest compression vs use of an automated chest compression device during resuscitation following out-of-hospital cardiac arrest: a randomized trial". JAMA 2006; 295(22):2620-2628.
Halperin, H. R., et al. "Cardiopulmonary resuscitation with a novel chest compression device in a porcine model of cardiac arrest: improved hemodynamics and mechanisms." J.Am.Coll. Cardiol. 44.11 (2004): 2214-20.
Halperin, M.D., Henry R., A Preliminary Study of Cardiopulmonary Resuscitation by Circumferential Compression of the Chest with use of a Pneumatic Vest, The New England Journal of Medicine, vol. 329 No. 11, Sep. 9, 1993, pp. 762-768.
Hostler D, Everson-Stewart S, Rea TD et al. "Effect of real-time feedback during cardiopulmonary resuscitation outside hospital: prospective, cluster-randomised trial". BMJ 2011; 342:d512.
Jenkins, Constance, et al., Effects of the ResQPOD on Kinetics, Hemodynamics of Vasopressin, and Survivability in a Porcine Cardiac Arrest Model, Military Medicine, vol. 180, Sep. 2015, pp. 1011-1016.
Kerber, R. E., J. D. Bourland, M. J. Kallok, P. Hite, B. Pritchard, F. Charbonnier, C. Birkett, K. Fox-Eastham, and R. A. Kieso. 1990. 'Transthoracic defibrillation using sequential and simultaneous dual shock pathways: experimental studies', Pacing Clin Electrophysiol, 13: 207-17.
Kerber, R. E., J. Grayzel, R. Hoyt, M. Marcus, and J. Kennedy. 1981. 'Transthoracic resistance in human defibrillation. Influence of body weight, chest size, serial shocks, paddle size and paddle contact pressure', Circulation, 63: 676-82.

(56) References Cited

OTHER PUBLICATIONS

Kerber, R.E., K.T. Spencer, M.J. Kallok, C. Birkett, R. Smith, D. Yoerger, and R.A. Kieso. 1994. 'Overlapping sequential pulses. A new waveform for transthoracic defibrillation', Circ, 89: 2369-79.
Kirchhof, P., L. Eckardt, P. Loh, K. Weber, R. J. Fischer, K. H. Seidl, D. Bocker, G. Breithardt, W. Haverkamp, and M. Borggrefe. 2002. 'Anterior-posterior versus anterior-lateral electrode positions for external cardioversion of atrial fibrillation: a randomised trial', Lancet, 360: 1275-9.
Kleinman, Monica E., et al., Part 5: Adult Basic Life Support and Cardiopulmonary Resuscitation Quality: 2015 American Heart Association Guidelines Update for Cardiopulmonary Resuscitation, and Emergency Cardiovascular Care, Circulation, 2015, 132, S414-S435.
Kouwenhoven, Jude; Knickerbocker, Cardiac Arrest—The Science and Practice of Resuscitation Medicine, (19600000), p. 96.
Kouwenhoven, W.B Closed-Chest Cardiac Massage, JAMA, Jul. 9, 1960, vol. 173, No. 10, pp. 1064-1067.
Lafuente-Lafuente et al., "Active chest compression-decompression for cardiopulmonary resuscitation (Review)," The Cochrane Collaboration, 2009, Issue 3 (40 pages).
Li, Y., H. Wang, J. H. Cho, W. Quan, G. Freeman, J. Bisera, M. H. Weil, and W. Tang. 2010. 'Defibrillation delivered during the upstroke phase of manual chest compression improves shock success', Crit Care Med, 38: 910-5.
Liao et al., "Manual versus mechanical cardiopulmonary resuscitation. An experimental study in pigs", BMC Cardiovascular Disorders, Oct. 2010, 10:53, http://www.biomedcentral.com/1471-2261/10/53 (8 pages).
Lurie et a., "Improving active compression-decompression resuscitation with an inspiratory impedance valve", originally published Mar. 15, 1995, https://doi.org/10.1161/01.CIR.91.6.1629, Circulation. 1995; 91:1629-1632.
Lurie et al., "Improving standard cardiopulmonary resuscitation with an inspiratory impedance threshold valve in a porcine model of cardiac arrest", Anesth Analg 2001; 93:649-655.
Lurie, K.G., Improving active compression-decompression cardiopulmonary resuscitation with an inspiratory impedance value, Abstract Circulation 1995; 91/6 (1 page abstract).
McClung, Christian D., et al.; Interposed Abdominal Compression CPR for an Out-of-Hospital Cardiac Arrest Victim Failing Traditional CPR; Oct. 20, 2015; Western Journal of Emergency Medicine; vol. XVI, No. 5; 690-692 (Year: 2015).
McDonald, M.D., John L, Systolic and Mean Arterial Pressures During Manual and Mechanical CPR in Humans, Annals of Emergency Medicine, 11:Jun. 6, 1982, pp. 292-295.
Michael, John R., et al., Mechanisms by with epinephrine augments cerebral and myocardial perfusion during cardiopulmonary resuscitation in dogs, Circulation 69, No. 4, 822-834, 1984.
Neumann T, Gruenewald M, Lauenstein C, Drews T, Iden T, Meybohm P. "Hands-on defibrillation has the potential to improve the quality of cardiopulmonary resuscitation and is safe for rescuers—a preclinical study". J Am Heart Assoc 2012; 1(5):e001313.
Niemann Md., James T., Cough-CPR, Documentation of systemic perfusion in man and in an experimental model: a window to the mechanism of blood flow in external CPR, Critical Care Medicine, vol. 8, No. 3, pp. 141-146, Mar. 1980.
Ong ME, Annathurai A, Shahidah A et al. "Cardiopulmonary resuscitation interruptions with use of a load-distributing band device during emergency department cardiac arrest". Ann Emerg Med 2010; 56(3):233-241.
Ong, M. E., et al. "Use of an automated, load-distributing band chest compression device for out-of-hospital cardiac arrest resuscitation." JAMA 295.22 (2006): 2629-37.
Paradis M.D., Norman A., Simultaneous Aortic, Jugular Bulb, and Right Atrial Pressures During Cardiopulmonary Resuscitation in Humans, Insights Into Mechanisms, Circulation, vol. 80, No. 2, Aug. 1989.
Paradis, N. A. "Is this the next step for CPR?" Am. J. Emerg. Med. 18 34.1 (2016): 97-99.
Paradis, N. A., et al. "Coronary perfusion pressure during external chest compression in pseudo-EMD, comparison of systolic versus diastolic synchronization." Resuscitation 83.10 (2012): 1287-91.
Paradis, Norman A., et al., Cardiac Arrest, The Science and Practice of Resuscitation Medicine, 2nd edition, Cambridge University Press 2007.
Plaisance et al., "Evaluation of an impedance threshold device in patients receiving active compression- decompression cardiopulmonary resuscitation for out of hospital cardiac arrest", Elsevier, Resuscitation 61 (2004) 265-271, www.elsevier.com/locate/resuscitation.
Plaisance P, Lurie KG, Payen D. "Inspiratory impedance during active compression-decompression cardiopulmonary resuscitation: a randomized evaluation in patients in cardiac arrest". Circ 2000; 101(9):989-994.

* cited by examiner

MULTIMODAL DEVICE AND METHOD TO INCREASE THE EFFICACY OF TRANSTHORACIC CARDIOVERSION OR CARDIAC PACING IN PATIENTS WITH PERFUSING RHYTHMS

RELATED APPLICATIONS

This application is a continuation-in-part of co-pending U.S. patent application Ser. No. 17/676,612, filed Feb. 21, 2022, entitled INCORPORATION OF THE ELECTRODES FOR DEFIBRILLATION INTO THE PATIENT-FACING COMPONENTS OF AUTOMATED CARDIOPULMONARY RESUSCITATION SYSTEMS, which is a continuation of co-pending U.S. patent application Ser. No. 16/514,968, filed Jul. 17, 2019, entitled INCORPORATION OF THE ELECTRODES FOR DEFIBRILLATION INTO THE PATIENT-FACING COMPONENTS OF AUTOMATED CARDIOPULMONARY RESUSCITATION SYSTEMS, which claims the benefit of U.S. Provisional Application Ser. No. 62/699,647, filed Jul. 17, 2018, entitled INCORPORATION OF THE ELECTRODES FOR DEFIBRILLATION INTO THE PATIENT-FACING COMPONENTS OF AUTOMATED CARDIOPULMONARY RESUSCITATION SYSTEMS, the entire disclosures of which are herein incorporated by reference.

FIELD OF THE INVENTION

The invention disclosed here relates in general to the field of medical devices. In particular, to devices and methods for improving the clinical outcome of patients suffering from cardiac dysrhythmias without cardiac arrest.

BACKGROUND OF THE INVENTION

Human beings may develop abnormal electrical rhythms of the heart without complete loss of hemodynamics, that is, without cardiac arrest. Among the most common is atrial fibrillation. Others include: atrial tachycardia, atrial flutter, ventricular tachycardia, and atrial, junctional or ventricular bradycardia, among others. In atrial fibrillation, atrial flutter, atrial tachycardia, and ventricular tachycardia, the heart rate may be too fast. In atrial, junctional, or ventricular bradycardia, it may be too slow. Ultimately, patients suffering these dysrhythmias may need an electrophysiologic procedure such as ablation or placement of a permanent pacemaker.

However, before those definitive procedures, there may be a need to terminate these abnormal electrical rhythms with an electrical therapy that can be external transthoracic cardioversion or pacing, also referred to as acute electrical therapy. Throughout this discussion, the terms transthoracic and transcutaneous may be used interchangeably, and have a similar meaning, specifically the application of electromagnetic energy to myocardium by means of transcutaneous transthoracic countershock or pacing from one or more cutaneous electrode locations. When the term countershock is utilized it is intended to mean the transthoracic application of electrical energy with the intention of terminating a dysrhythmia such that a more normal cardiac rhythm is restored. Termination of atrial fibrillation has been called defibrillation. However, given that the intent of therapy for dysrhythmias is to convert the heart rhythm to a supraventricular organized regular perfusing rhythm, terms such as cardioversion are more accurate. The term defibrillation is often used in regard to countershock technology, and the equipment is often referred to as defibrillators, however, the terms countershock or cardioversion are more accurate. The term countershock refers to an electrical shock being applied to the heart. A device that is intended to enhance the probability that electrical cardioversion has occurred successfully and the heart has been changed from a certain state of dysrhythmia to a more organized rhythm is best described as a cardioverter. With respect to transthoracic pacing of the heart, the terms pacer, pacemaker are used interchangeably.

Both cardioversion and pacing are forms of Acute Electrical Therapy (AET), and as used herein, the terms electrical therapy, acute electrical therapy, and countershock can refer to cardioversion and/or pacing. Both cardioversion and pacing can work by delivering an electric shock through the thorax of a patient, also referred to as transthoracic cardioversion or pacing. Either form of acute electrical therapy can be delivered by a device that can be referred to as a Transthoracic Cardioverter Pacer (TCP). In some cases, a TCP can be a cardioverter that delivers electrical therapy in the form of cardioversion. In some cases, a TCP can be a pacer that electrical therapy in the form of pacing. In some cases, a TCP can provide cardioversion and/or pacing in different situations. As used herein, the term TCP can refer to a pacer, a cardioverter, or a combination pacer and/or cardioverter that can function as a pacer or a cardioverter in different situations.

Detection, recording, measurement, and analysis of the electrocardiogram (ECG) is centrally important in detection and management of atrial fibrillation and other dysrhythmias, as taught in U.S. Pat. No. 4,184,493 to Langer, titled CIRCUIT FOR MONITORING A HEART AND FOR EFFECTING CARDIOVERSION OF A NEEDY HEART, and U.S. Pat. No. 4,559,946 to Mower, titled METHOD AND APPARATUS FOR CORRECTING ABNORMAL CARDIAC ACTIVITY BY LOW ENERGY SHOCKS, the entire teachings of which are both incorporated herein by reference. Said measurement may be an input into an analysis and control device, which may be standalone or a component of a multimodal device.

The success of external cardioversion, countershock and transthoracic pacing is principally associated with improved current flow across or through the myocardium, which is itself a function of electrical potential, along with transthoracic and transcardiac resistances when using a direct current. Decreasing resistance is associated with improved current flow, and techniques which lower transthoracic resistance would generally increase the success of transthoracic countershock or pacing. The equivalent of transthoracic resistance when using alternating current is transthoracic impedance, and measurement of transthoracic impedance with a small current may be used as a surrogate indicator of transthoracic resistance.

Current flow through the chest during transthoracic countershock or pacing may not be linear from one electrode to another, but may also be nonlinear as a function of tissue and organ resistance, capacitance, or impedance. This pattern may be affected by mechanical processes such as chest compression, constriction, ventilation status, visceral organ hydration status, patient specific anatomy, and other factors (see below). Air is an insulator, so the ventilatory cycle of the lungs may affect transthoracic resistance and electrical countershock.

Different tissues have varying capacities for current flow, and this affects placement of electrodes. Of particular importance is the poor capacity of bone and air to carry current. Thus, skeletal structures, and the lungs tend to be avoided when applying electrodes externally.

Although multiple mechanical and physiologic alterations have been identified as means to enhance the efficacy of countershock or pacing, these techniques are rarely used. Currently, almost all transthoracic countershock or pacing is done via self-adhesive electrode pads. Little effort beyond alteration of electrical discharge itself or placement of the electrodes has been made to enhance the efficacy of transthoracic countershock or pacing.

Non-Electrical Means to Enhance Countershock

In some studies, the performance of countershock can be improved by using an anterior-posterior vector. (Kirchhof et al. 2002). In this scenario, one paddle is placed in the front of the patient, and another is placed posteriorly between the shoulder blades. Additionally, the efficacy of electrical countershock or pacing may be improved by application of multiple transthoracic pathways that are electrified near simultaneously or sequentially, as described in U.S. Pat. No. 9,174,061 to Freeman, titled MULTI-PATH TRANSTHORACIC DEFIBRILLATION AND CARDIOVERSION, the entire teachings of which are incorporated herein by reference. The efficacy of electrical countershock may be significantly improved by application of countershock via multiple positive-negative electrode pairs, as described in U.S. Pat. No. 4,708,145 to Tacker Jr., titled SEQUENTIAL-PULSE, MULTIPLE PATHWAY DEFIBRILLATION METHOD, the entire teachings of which are incorporated herein by reference. It is also known that changing the direction of current flow during the countershock or pacing may enhance efficacy.

Application of Force to Electrodes—Transthoracic resistance to current flow may be lowered with the application of force on paddles or gel pads—previously called paddle contact pressure. The transition from paddles to self-adhesive gel electrode pads may actually have negatively affected this parameter. The application of force on countershock paddles or electrodes, also referred to as paddle contact pressure, can result in a lowered transthoracic resistance to current flow. (Kerber et al. 1981). An increase in countershock paddle force can be associated with a decrease in transthoracic resistance and an increase in peak current. Clinically, the force that was historically applied manually to paddles to enhance contact force pressure and lower resistance tended to range between 90 and 250 Newtons.

The transition from paddles to adhesive gel pads may have negatively affected this parameter because providers did not physically apply contact pressure to the gel pads. It has been found that applying force to the adhesive gel electrodes can also lower transthoracic impedance, thereby improving it. (Ramirez et al. 2016). When paddle electrodes were being used, practitioners would apply force to enhance contact pressure and lower resistance. It has even been advised that clinicians apply a force similar to a "push-up" at the moment of electrical discharge. Various practitioners have demonstrated that applying force to the adhesive gel electrodes lowers transthoracic impedance and increases current flow across the myocardium. Such effects are associated with a greater fraction of dysrhythmia patients being successfully cardioverted or paced.

Ventilatory Cycle—Air is an insulator, so the ventilatory cycle of the lungs may affect electrical countershock by means of affecting transthoracic resistance. It has been found that an association exists between the ventilatory cycle and transthoracic impedance. (Ewy et al. 1980). An association has been found between the ventilatory cycle and transthoracic impedance, with higher transthoracic impedances with inspiration, and a significant decrease in countershock success when shocks were delivered in inspiration compared to expiration. Physiologically, electrical countershock may be more effective if it is timed to synchronize with the lungs at maximal expiration.

While control of the ventilatory cycle is straightforward in intubated patients receiving mechanical ventilation, placing the thorax in exhalation to advantage countershock or pacing may be more difficult in patient not under the control of mechanical ventilation.

Previously, others have achieved partial exhalation using transcutaneous functional electrical stimulation (FES). FES is the application of electrical pulses to the motor nerve of a muscle causing the muscle to contract, as described in US Patent Publication No. 2002/0128686 to Minogue, titled ELECTROTHERAPY DEVICE AND METHOD, the entire teachings of which are incorporated herein by reference. Transcutaneous FES has been used to assist respiratory function. FES of the abdominal muscles, in particular the rectus abdominis, acts to assist exhalation Vibrational or Acoustic Energy—An additional non-electrical transthoracic mechanism that may affect the status of the myocardium is application vibrational or acoustic energy. Acoustic, ultrasound and vibrational energy are the same in nature and differ only in their frequencies. As used herein, the term vibrational energy can include both acoustic and ultrasound energy. This technique has been proposed as: 1) a sole-therapy alternative to electrical countershock, as discussed in U.S. Pat. No. 7,006,864 to Echt, titled METHODS AND SYSTEMS FOR VIBRATIONAL TREATMENT OF CARDIAC ARRHYTHMIAS, the entire teachings of which are incorporated herein by reference, and 2) as a means for transthoracic pacing (Towe 2006), and 3) as means for both defibrillation and pacing, as disclosed in US Patent Publication No. 2010/0094149 to Kohut, titled NON-INVASIVE ULTRASOUND CARDIAC PACEMAKER AND DEFIBRILLATOR, the entire teachings of which are incorporated herein by reference. Ultrasound is a type of acoustic energy which is widely used for imaging and therapy in medicine. In particular, it is utilized for imaging of the heart. It has also been appreciated that acoustic, ultrasound or vibratory energy might be combined with electrical energy to more efficiently and effectively achieve defibrillation or pacing, as described in U.S. Pat. No. 7,809,438 to Echt, titled METHODS AND SYSTEMS FOR TREATING ARRHYTHMIAS USING A COMBINATION OF VIBRATIONAL AND ELECTRICAL ENERGY, the entire teachings of which are incorporated herein by reference.

The optimal parameters of acoustical energy for transthoracic countershock or pacing are shown in U.S. Pat. No. 7,006,864, Table 3 to have efficacy optima. More specifically, there were optimal patterns with respect to: Frequency (MHz) Burst length (cycles), Burst rate (Hz), Duty cycle (%)Duration (msec) and Myocardial Coverage (%).

| Parameter | Cardioversion and Defibrillation Preferred Implementation | Cardioversion and Defibrillation Most Preferred Implementation | Cardioversion and Defibrillation Most Preferred Implementation | Pacing Most Preferred Implementation |
|---|---|---|---|---|
| Frequency (MHz) | 0.020-10.0 | 0.050-1.00 | 0.100-0.300 | 0.25-0.50 |
| Burst length (cycles) | <5000 | <500 | <50 | <50 |
| Burst rate (Hz) | >10 | ≥100 | ≥100 | Single burst |
| Duty cycle (%) | <50 | <10 | <5 | 100 |
| Duration (msec) | <200 | <50 | <20 | <0.20 |
| No. of cardiac cycles | as required | <5 | <15 | All |
| MI | <50 | <25 | <15 | <2 |
| TI | <4 | <1 | <1 | <0.1 |
| Myocardial Coverage | >50 | >75 | <90 | <20 |
| Cardiac cycles from sense to trigger | <10 | <5 | <2 | 0 or 1 |

In using acoustical or vibratory energy for countershock or pacing, it is generally believed that the acoustic energy should be directed such that it engages the largest possible fraction of the cardiac anatomy involved in the dysrhythmia. Avoidance of bony structures, such as the sternum or ribs, or air containing structures such as the lungs, may be associated with greater acoustical energy reaching the myocardium. However, vibrational or acoustic mechanisms to achieve countershock or pacing may be less effective than electrical countershock and has not been developed for use clinically.

Nerve Stimulation: Vagal nerve stimulation for the treatment of numerous medical conditions is widely known, and it has already been recognized that vagal nerve stimulation may be used to prevent or treat atrial fibrillation and other cardiac rhythm disorders, as taught in US Patent Publication No. 2013/0131746 to Simon, titled NON-INVASIVE VAGUS NERVE STIMULATION DEVICES AND METHODS TO TREAT OR AVERT ATRIAL FIBRILLATION, the entire disclosure of which is incorporated herein by reference. When undertaken noninvasively, vagal nerve stimulation can be accomplished transcutaneously by means of electrical stimulation. However, it is also possible to stimulate the vagal nerve by means of acoustic, ultrasound or vibratory energy. (see Yap et a12020 the entire teachings of which are incorporated herein by reference).

It is also well known that stimulation of the vagus nerve is inhibitory of the cardiovascular system in general and the transcutaneous stimulation of the vagus nerve may be utilized for treatment of atrial fibrillation in particular. This may be done transcutaneously at the ear or neck. As a specific example, transcutaneous electrical stimulation of the auricular branch of the right vagus nerve at the tragus of the ear has been demonstrated to suppress atrial fibrillation. Anatomical studies of the ear indicate that the tragus, concha, and cymba concha may be used for vagal nerve stimulation. Alternatively, the nerve may be electrically stimulated transcutaneously at the neck, with electrodes placed near the sternocleidomastoid muscle.

ECG Predictors of Countershock Success: Treatments for atrial fibrillation have risks associated with them. Pharmacological cardioversion (termination of the dysrhythmia with drugs) exposes the patient to the toxicities of the drugs. Principal among these is QT prolongation, which can degenerate to Torsade de pointes, which is hemodynamically unstable. There is an old adage that every antiarrhythmic may also be proarrhythmic. In some respects, electrical cardioversion may appear safer because it is not associated with these pharmacologic risks. However, the pain of cardioversion, and in some cases transthoracic pacing, requires the use of sedation or even general anesthesia, which have significant inherent risks. Because of these inherent toxicities, there has been some effort to identify methods to predict the likelihood of efficacy.

Zeemering et al. (The electrocardiogram as a predictor of successful pharmacological cardioversion and progression of atrial fibrillation 2017) studied the predictive power of various metrics of atrial fibrillation. They considered both clinical patient descriptions (weight, heart volume, etc.) and ECG-derived measurements which had "appeared frequently in the last decade of non-invasive AF complexity literature." They concluded that the predictive power of the ECG metrics were generally "superior" to the clinical metrics, but that only a few of these ECG metrics were useful. The best predictions were yielded by combining ECG metrics with classic metrics of patient physiology.

Zeemering et al. conducted a statistical analysis of the predictive power of all possible combinations of ECG metrics, and showed the best-performing parameter combination included DF(II), SE(1),FWA(aVF,V1), MOI(V(3+4), V(3+5)). "Lead" refers to which of the twelve ECG electrodes on the patient the signal comes from. The best model in the first of five categories, single lead frequency domain, uses the dominant frequency at lead 2, the organization index at lead 3, and the spectral entropy at lead 1. It has an AUC of 0.72. Zeemering et al also listed the best-performing single metric (Spectral Variability), the best-performing metric (single or combination) from a single lead (Dominant Frequency at lead 2, Organization Index at lead 3, and Spectral Entropy at lead 1), and the best-performing single metric from a single lead (Dominant Frequency at lead 2). None of these outperform the "Combined" parameter model.

Current Techniques Often Ineffective—While transthoracic electrical countershock or pacing are often effective in terminating dysrhythmias in patients with perfusing hemodynamics, these therapies are not always successful. In almost every series cases published, approximately 10% of patients in whom transthoracic cardioversion is attempted electrically remain in the dysrhythmia. The rate at which transthoracic pacing fails is not as well known, but failure to capture the heart electrically and or mechanically is quite common. These significant failure rates are despite significant effort at improving the transthoracic countershock or pacing electrical waveform.

Failed transthoracic cardioversion is problematical in part because patients need to be sedated because of the pain caused by the electrical discharge. When the dysrhythmia is not terminated, the patient remains in a pathological circulatory state and has been subjected to the risks of sedation without benefit. When transthoracic pacing fails to capture the myocardium, the patient may be left hypotensive and require emergency placement of a transvenous pacer.

It would be desirable to have a device for use during countershock or pacing of patients not in cardiac arrest that can enhance the efficacy of cardiac countershock or pacing through the application of various multimodal systems.

SUMMARY OF THE INVENTION

This present disclosure overcomes disadvantages of the prior art by providing a method, apparatus, and multimodal system to improve the efficacy of transthoracic cardioversion or pacing in patients with a perfusing circulation. This may be achieved by a method and/or device that integrates automatic mechanical, pneumatic, acoustic and electrophysiologic capabilities with electrical countershock or pacing capabilities such that the probability of successful cardioversion is increased. The sequence, forces, and electrical properties of the subsystems can be computer controlled. The control system may use pre-defined a priori sequences or may optimize all components based on biomarker or subsystem status feedback. As used herein, "a priori" refers to parameters, conditions, timing, sequences, etc. that have been previously determined to be effective, and can be pre-programed into the device so that they can be applied by the device immediately and automatically at the beginning of treatment. As used herein, "optimization" refers to the process of improving parameters in an iterative process that works towards ideal parameters. Optimization can mean iteratively adjusting and updating various parameters in response to biomarkers or other data collected from sensors that can be part of afferent limbs and/or effector limbs, explained more fully below.

As such, the device is intended to enhance the acute efficacy of both the cardiac electrical therapies of cardioversion (including defibrillation) and pacing by means of synchronizing adjunctive interventions. Such a device and/or method may be called an Cardiac Electrical Therapy Efficacy Enhancement System (CETEES). Devices and subsystems intended to achieve cardioversion or defibrillation will, for the purposes of this description, be referred to as cardioverters. Devices and subsystems intended to capture and achieve cardiac peacemaking will, for the purposes of this description, be referred to as pacers or pacemakers interchangeably. In various embodiments, the electrical subsystem that delivers an electric shock intended to achieve cardioversion or pacing of the heart may be combined into a single cardioversion-pacemaker subsystem that can be referred to as a Transthoracic Cardioverter Pacer (TCP). As used herein, the term TCP can describe a cardioverter, a pacemaker, and/or a combined cardioverter and pacemaker that have been combined into a single system capable of either function. The patterns of electrical discharge from such a subsystem may be determined by a connected controller.

Because multiple interventions may enhance countershock or pacing, a multimodal device may be utilized. Multimodal medical devices may have an overall structure that includes biomarker based afferent limbs, control modules, and effector limbs. During dysrhythmias, it is common to measure one or more biomarkers chosen from a list that includes: ECG, ECG derived biomarkers such as fast-Fourier transform based power spectra, ET-CO2, indicators of tissue oxygenation or energetics (i.e. NIRS), indicators of hemodynamics such as photoplethysmography, among others.

Most electromechanical medical devices have control modules that may be similar to a modern digital computer, or may be operator based. Afferent limbs may be subsystems that provide measurements to the control module. Afferent limbs can also be referred to as afferent subsystems. Afferent limbs inputting to the control module may include measurements of clinically relevant biomarkers such as ECG, cardiovascular photoplethysmography, measure of ventilatory status, and others. Effector limbs may also be referred to as effector subsystems. Effector limbs may be those subsystems that affect the status of the patient in some manner. The overall system may be closed loop in which the effect of the effector subsystems is measured by the afferent limb and the control module subsequently adjusts the effector subsystems.

The present disclosure overcomes disadvantages of the prior art by enhancing the efficacy of transthoracic countershock or pacing using self-adhesive gel electrode pads by means of increased contact pressure, synchronization with ventilation, utilization of multiple current paths, vibrational or acoustic energy, vagal stimulation or other mechanical or physiological means. Although the present disclosure includes descriptions of countershock or pacing electrodes as being self-adhesive gel electrode pads, it should be clear that the present disclosure also apples to non-adhesive and/or non-gel electrodes, and the disclosure is not intended to be limited to only self-adhesive gel electrode pads.

The present disclosure can provide an easily utilized device and method to adjunctively improve the efficacy of transthoracic countershock or pacing in patients suffering cardiac dysrhythmia by means of adding one or more of the following:

- electromechanical and physiologic optimization, including optimization that is separate from changes in waveform, voltage or current;
- integration and optimization of one or more adjunctive techniques;
- enhanced contact force pressure;
- application of acoustic, ultrasound or vibratory energy;
- optimization of thoracic anatomy;
- optimization of ventilatory cycle;
- stimulation of the vagal system;
- various combinations of optimizations;
- a device that applies these various optimization automatically; and
- a device that integrates these optimizations along with multipath countershock or pacing.

DETAILED DESCRIPTION

This Cardiac Electrical Therapy Efficacy Enhancement System (CETEES) described herein includes a method and devices to adjunctively enhance the efficacy of transthoracic electrical cardioversion or pacing in patients with perfusing circulations. This can be achieved by the multimodal system that integrates automatic mechanical, pneumatic, acoustic and/or electrophysiologic capabilities with electrical countershock or pacing capabilities such that the probability of successful cardioversion or is increased. The CETEES described herein can enhance efficacy of self-adhesive gel electrode pads for transthoracic countershock or pacing by means of integrating increased contact pressure, synchronization with ventilation, utilization of multiple current paths, vibrational or acoustic energy, vagal stimulation and/or other mechanical or physiological means.

As described, although multiple anatomic, physiologic, and mechanical mechanisms are available to enhance the efficacy of transthoracic cardioversion or pacing in patients with a perfusing circulation, these potential adjuncts have not been utilized clinically principally because there has not been an easily utilized method or device for their application.

Figure 1:
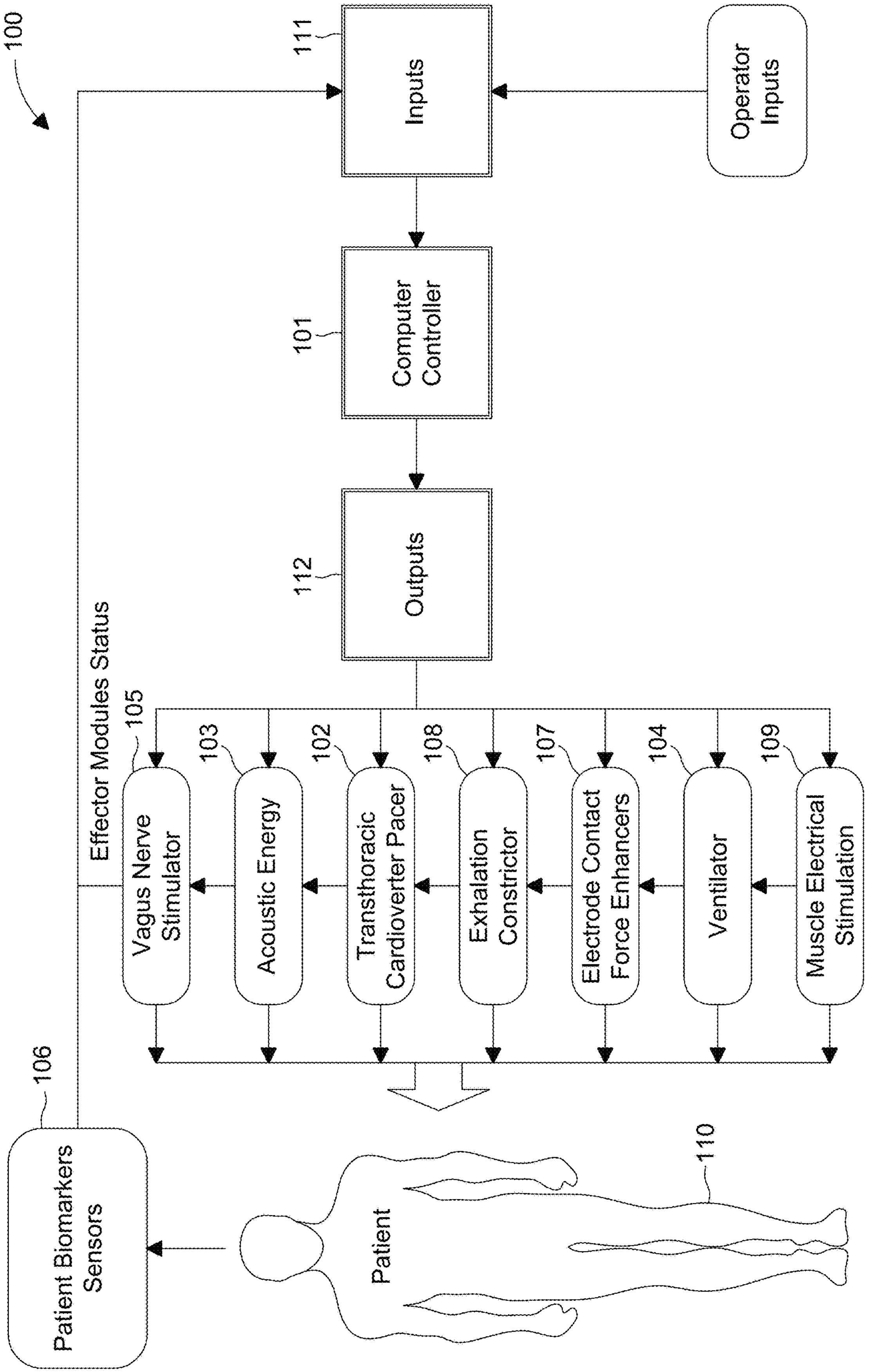
FIG. 1 is a schematic diagram of a Cardiac Electrical Therapy Efficacy Enhancement System (CETEES), showing subsystem interactions with a schematic patient and the flow of subsystem and biomarker inputs and outputs, according to an illustrative embodiment.

FIG. 1 is a schematic diagram of a CETEES 100, showing subsystem interactions with a schematic patient and the flow of subsystem and biomarker inputs and outputs, according to an illustrative embodiment. The sequence, forces, and electrical properties of the subsystems can be controlled by computer controller 101. Computer controller 101 can also be referred to as a processor 101 or a control system 101. A CETEES can be controlled by a processor 101 that can include a plurality of modules, data inputs, and control outputs, and a user interface. The processor can be contained within a general purpose, or a dedicated, computing device, such as a PC, laptop, tablet or smartphone. In various embodiments, the computing device can be built into, or incorporated within, the housing of the CETEES. The computing device can include a user interface that can be a keyboard, mouse, touch screen or similar device, and a display that can include a graphic user interface screen. In practice, a user can input instructions for a procedure through the user interface into the processor. The modules and/or sub-modules can then process the instructions, collect measurements, and provide information to the various subsystems of the CETEES.

The control system 101 may use pre-defined a priori parameters and/or sequences, and/or the control system may optimize all components based on biomarker or subsystem status feedback. In various embodiments, the CETEES can start with a priori parameters and/or sequences, and can optimize those parameters and/or sequences during treatment in response to biomarker or subsystem status feedback. The parameters and/or sequences can be optimized, or adjusted, as treatment is ongoing to provide customized individual treatment that is adapted in real time to each patient in order to provide superior treatment to that patient. The controller 101 can provide outputs 112 from the controller 101 to the various subsystems to control the subsystems.

By way of non-limiting example, an embodiment of a CETEES 100 can integrate gel electrode pads with one or more additional subsystems. The CETEES 100 can include one or more cardioverter(s) and/or pacemaker(s) that can also be referred to as Transthoracic Cardioverter Pacers (TCPs) 102. The TCP 102 can apply shocks to the patient through electrode pads. In various embodiments, the electrode pads can be gel electrode pads or self-adhesive gel electrode pads. The controller 101 can provide outputs 112 from the controller 101 to the TCP 102 which can control the TCP 102 to provide electric shocks through the electrodes to the patient 110.

The CETEES 100 can include electrode contact force enhancers 107. The electrode contact force enhancers can apply force that presses electrodes against the patient. This results in increased contact pressure, i.e. applying force to the pads or paddles. The increased contact pressure can reduce impedance, thereby improving the likelihood of successful cardioversion. In various embodiments, the controller can control the contact force enhancers to provide increased contact pressure during pacing. In various embodiments the controller 101 can control the contact force enhancers 107 to provide increased contact pressure before the shock is delivered, and reduce contact pressure after the shock is delivered. In various embodiments, the controller 101 can control the contact force enhancers 107 to reduce contact pressure between shocks, and increase contact pressure during shocks.

The CETEES 100 can include a vagus nerve stimulator 105. The vagus nerve stimulator 105 can provide stimulation to the vagus nerve of the patient. The controller 101 can control the vagus nerve stimulator 105. In various embodiments, the stimulation of the vagus nerve can be transcutaneous, for example, at the ear or neck. In various embodiments, the stimulation of the vagus nerve can be electromagnetic and/or acoustical.

The CETEES 100 can include a myocardium energy emitter 103 that can direct energy towards the myocardium of the patient. The myocardium energy emitter 103 can emit acoustic energy towards the myocardium of the patient 110. The acoustic energy emitted towards the myocardium can be ultrasound energy.

The CETEES can include one or more subsystems that can help to reduce the volume of air in the lungs for pacing shock delivery. In various embodiments, the CETEES can include a ventilator 104, an exhalation band 108, such as a constrictor band, and/or a muscle electrical stimulator 109. The exhalation band 108 may be either mechanical or pneumatic in nature, and mechanical exhalation bands and/or a pneumatic exhalation bands can both be referred to as an exhalation band 108. The controller 101 can provide output instructions 112 to the ventilator 104 so that the controller can coordinate the ventilator with the delivery of pacing shocks, thereby helping to coordinate so that pacing shocks can be delivered at a minimal lung volume.

The controller 101 can provide output instructions to the exhalation band 108 which can constrict the torso of the patent 110 to reduce the volume of air in the lungs. The controller can coordinate the exhalation band with the delivery of pacing shocks, thereby helping to coordinate so that pacing shocks can be delivered at a minimal long volume.

The controller 101 can provide output instructions to the muscle electrical stimulator 109 which can stimulate the rectus abdominus muscle, thereby causing the patient to exhale. The controller can coordinate the muscle electrical stimulator 109 with the delivery of pacing shocks, so that the patient is stimulated to exhale and reduce the volume of air in the lungs for the delivery of a pacing shock.

In various embodiments, some, all, or none of the subsystems may be incorporated in a single unit with the controller. In various embodiments, the CETEES may be a single unit with multiple subsystems. In various embodiments, the controller may be connected to, and provide controlling output instructions to various subsystems that may be separate components or components that may otherwise be capable of operating separately. Regardless of the extent or degree of connection between the controller and the various subsystems, the CETEES can coordinate each of the subsystems to work together to provide coordinated treatment and improved likelihood of successful cardioversion. In various embodiments, various cables, hoses, wireless connections, and/or other connections can exist between the controller and the various subsystems so that the controller can control and coordinate the various subsystems.

The various subsystems of the CETEES can provide feedback in the form of inputs 111 to the controller 101. The inputs can include the status of various subsystems, such as readiness to deliver a shock, exhalation status, and others. The CETEES can include various sensors, including biomarkers, ECG, photopleth, ventilation, and/or other sensors. The various sensors can provide patient biomarker data 106 that can be used as inputs 111 to the controller 101 about the status of the patient. The controller 101 can adapt the treatment of the patient in response to the various inputs. The controller can provide outputs 112 that control and coordinate the various subsystems.

Various methods of improving patient outcome can be adjunctive to the countershock treatment provided by the TCP 102. The controller 101 and various subsystems can adjunctively provide additional benefit to the patient, or increase the likelihood of successful cardioversion by various means, including, but not limited to:

- Increased contact pressure, i.e. applying force to the pads or paddles.
- Synchronization with ventilation, i.e. applying the current at an optimal phase of the ventilatory cycle (Deakin et al. 1998). Specifically, application of the transthoracic cardioversion or pacing electrical current at or near the time of maximum ventilatory exhalation.
- Varying the combination, location, or current pathways of the electrode pads or paddles. By way of non-limiting example, this can include using multiple paths across the chest and can include applying two counter shocks simultaneously at a 90° angle to one another.
- Altering the anatomic conformation of the thorax to minimize resistance to current flow across the myocardium. By way of non-limiting example, this can include decreasing the anterior to posterior dimension of the chest. In various embodiments, decreasing the anterior to posterior dimension of the chest can be accomplished by applying contact force to electrodes on the front and back of the thorax of the patient. In various embodiments, decreasing the anterior to posterior dimension of the chest can be accomplished by constricting an exhalation band 108 that is around the thorax of the patient. In various embodiments, decreasing the anterior to posterior dimension of the chest can be accomplished by decreasing the lung volume of the patient through control of a ventilator 104 and/or a muscle electrical stimulator 109.
- Placing the myocardium into a state more amenable to cardioversion or pacing by means of applying acoustic, ultrasound or vibratory energy.
- Application of vagal nerve stimulation.

The controller can adjunctively improve the efficacy of transthoracic countershock or pacing by means of:

- electromechanical and physiologic optimization separate from changes in waveform, voltage or current;
- integration and optimization of one or more adjunctive techniques;
- enhanced contact force pressure;
- application of acoustic, ultrasound or vibratory energy;
- optimization of thoracic anatomy;
- optimization of ventilatory cycle;
- stimulation of the vagal system;
- a combination of optimizations;
- application of these various optimization automatically;
- integration of various optimizations along with countershock or pacing; and/or
- integration of various optimizations along with multipath countershock or pacing.

Figure 2:
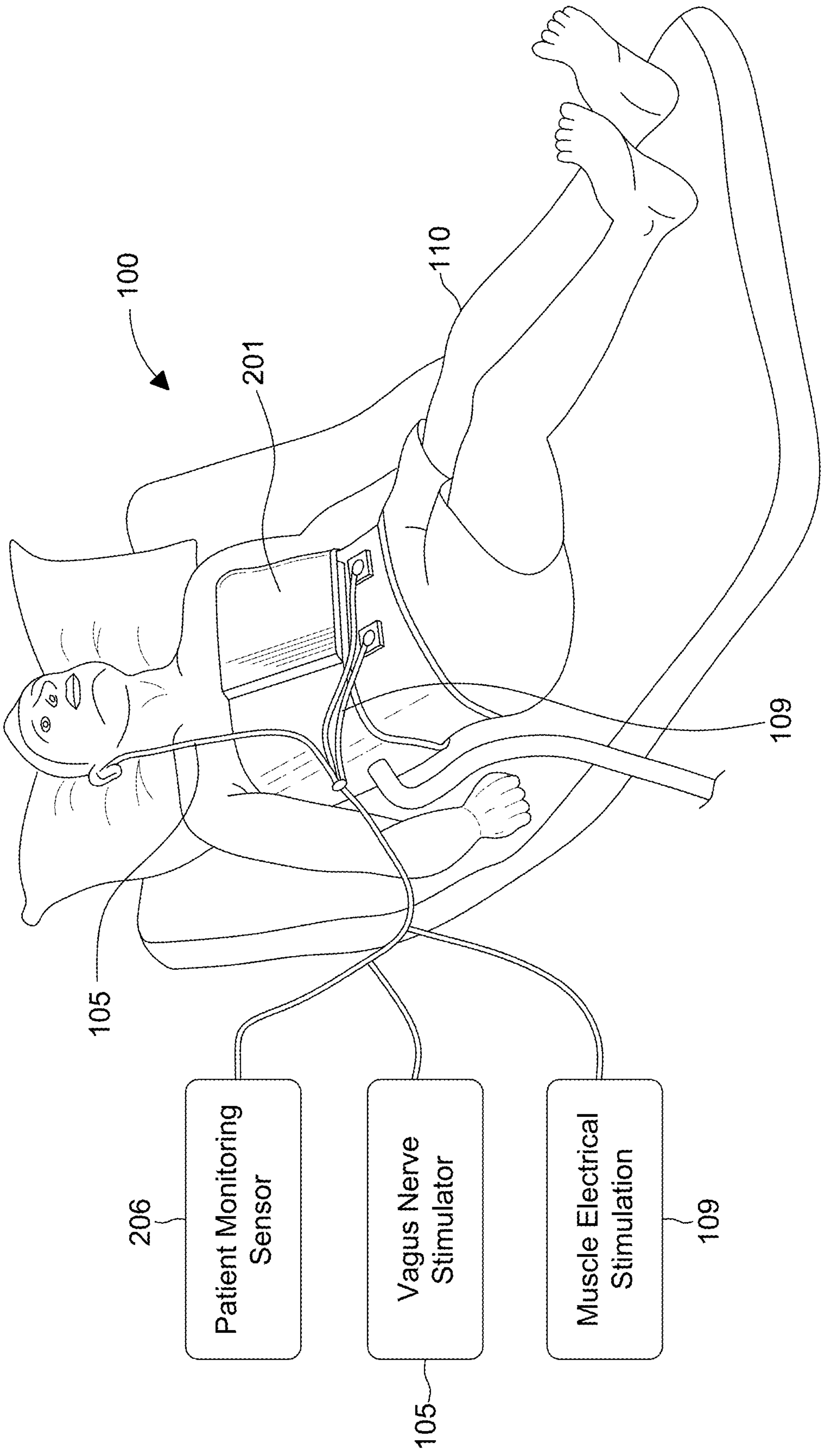
FIG. 2 is a perspective view of the CETEES applied to a patient, according to an illustrative embodiment.
Figure 3:
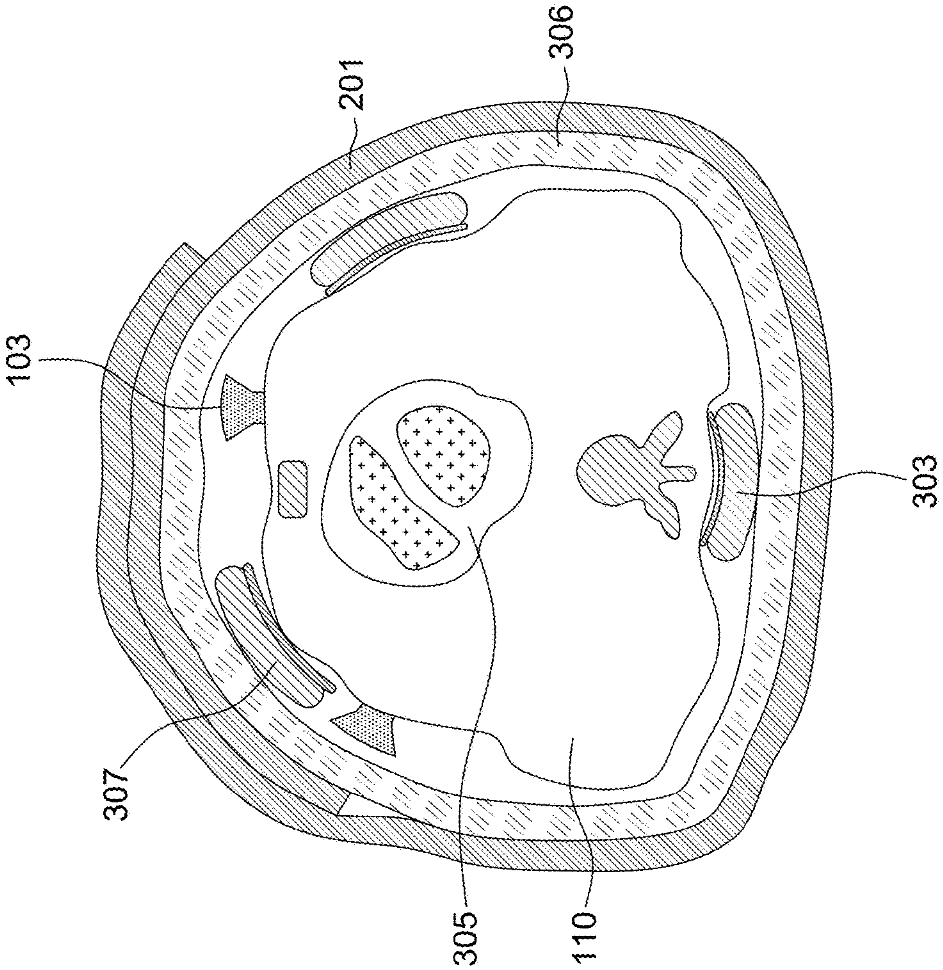
FIG. 3 is a partially cut-away view of the CETEES around a patient's thorax, showing inner workings including countershock or pacing electrode pads and contract force enhancers, according to an illustrative embodiment.

FIG. 2 is a perspective view of the CETEES applied to a patient, according to an illustrative embodiment, and FIG. 3 is a partially cut-away view of the CETEES around a patient's thorax, showing inner workings including cardioversion pads and contract force enhancers, according to an illustrative embodiment. As used herein, cardioversion pads can also be referred to as pacing pads, TCP pads, or countershock pads, and the terms can be used interchangeably throughout this document. Turning to FIGS. 2 and 3, the CETEES can include an inelastic outer shell 201 that can contain and maintain the location and orientation of various patient facing subsystems. This shell also provides a structure against which patient-facing components may push so as to allow counter-force to be directed inward toward the patient. This can include providing counterforce for the contact force enhancers 303 so that they can press the electrode pads 302 against the patient. This shell may be vest-like in shape and adjustable for patients of varying size and circumference. There can be a closure mechanism such as hook and loop tape, buckles, or other closures In various embodiments, the electrode pads 302 can be gel electrode pads, and can be self-adhesive gel electrode pads. In various embodiments, the contact force enhancers 107 can be inflatable bladders 303 that can selectively apply force to electrode pads 302, and can be hydraulic or pneumatic. In various embodiments, the contact force enhancers 107 can be solenoids or other mechanical pushing mechanisms 307 that can selectively apply force to electrode pads 302. In various embodiments, the contact force enhancers 107 can include a circumferential constrictor 306 that can be a circumferential bladder, multiple circumferential bladders, a constrictable inelastic belt, or various other circumferential constrictors. In various embodiments, the contact force enhancers 107 can include various combinations of different types of contact force enhancers. In various embodiments, the contact force enhancers 107 can all be the same type of force enhancer or multiple types of force enhancers.

The CETEES can include an exhalation constrictor band 108 that can squeeze the torso of the patient, thereby decreasing air volume in the lungs and changing the conformation of the torso to bring the anterior and posterior of the torso closer together. The exhalation constrictor band 108 can include one or more bladders that can inflate to squeeze the patient, similar to a blood pressure cuff. In various embodiments, the exhalation constrictor band 108 can include multiple bladders arranged in parallel around the patient. The exhalation constrictor band 108 can be inside of the inelastic shell 301, and the shell 301 can provide a counterforce so that the bladders can press against the patient as they inflate. In various embodiments, the inflatable bladder(s) of the exhalation constrictor band 108 can be hydraulic or pneumatic. In various embodiments, the exhalation constrictor band can be a mechanical device that tightens an inelastic belt around the patient to squeeze the torso of the patient. In various embodiments, the exhalation constrictor band 108 can also be the circumferential constrictor 306 of the contact force enhancer 107, or the CETEES can have distinct and separate exhalation constrictor band 108 and contact force enhancer circumferential constrictor 306. In various embodiments, one or more components of the one or more contact force enhancers 107 can act as and/or can work to assist the exhalation constrictor band 108.

The CETEES 100 can include one or more acoustic energy emitters 103 that can transmit acoustical, ultrasound, or vibratory energy to the myocardium. In various embodiments, the acoustic energy emitter 103 can be an ultrasound emitter. The CETEES 100 can include one or more vagus nerve stimulators 105 which can stimulate the vagus nerve transcutaneously using electromagnetic and/or acoustic stimulation. The CETEES can also include transcutaneous muscle stimulation electrodes 109. Transcutaneous muscle stimulation electrodes 109 can stimulate the rectus abdominus muscle to cause the patient to exhale.

The CETEES 100 can also include a number of sensors 206 that can collect patient biomarker data. These sensors can include ECG, photopleth, ventilation sensors, and/or various other sensors. Sensors 206 can provide patient biomarker data 106 as inputs 111 to the controller 101.

CETEES Countershock or Pacing

Within the context of the device disclosed herein, the TCP 102 can have a significantly expanded spectrum of capabilities. It can do more than simply charge the electrodes 302 and release current from the storage capacitors. It can further interface with the control processor, provide input 111 status data to the controller 101 and receive output 112 instructions from the controller 101. It can countershock or provide pacing via multiple electrode pairs, as described in U.S. Pat. No. 4,708,145.

In various embodiments, the CETEES 100 may incorporate transthoracic pacing subsystems 102, or may be a separate unit from the transthoracic pacing subsystems and connected to them via outputs 112 from the controller 101.

The efficacy of the function of the TCP 102 can be adjunctively enhanced by inclusion of, and coordination with, one or more other subsystems that can include the contact force enhancers 107, the acoustic, ultrasound or vibratory energy emitter 103, the ventilator 104, the muscle electrical stimulator 109, and/or the vagal nerve simulator 105.

Multiple Paths

A CETEES system may allow current to be released from one or more combinations of electrodes 302. The use of multiple combinations of electrodes 302 can include using multiple paths across the chest, as is described in U.S. Pat. No. 9,174,061. The use of multiple paths across the chest can include applying two or more counter shocks simultaneously along paths that are at an angle to each other. In various embodiments, two counter shocks can be delivered simultaneously along paths that can be at a 90° angle to one another. With respect to the countershock subsystem, multiple electrode pads 302 can be used to create multiple transthoracic pathways through the patient. Electric current can be directed through selected countershock electrodes 302 to create various transthoracic pathways through the patient. As used herein, countershock electrodes can also be referred to as defibrillation electrodes, pacing electrodes, cardioversion electrodes, or TCP electrodes, and the terms can be used interchangeably throughout this document. Incorporation of the cardioversion electrodes 302 into the patient facing surfaces of the CETEES allows for multiple countershock subsystems 102 to be discharged simultaneously or sequentially, and allows for the use of one or more transthoracic pathways between various cardioversion electrodes 302. Various embodiments described herein can include incorporating a dual/triple/(N) sequential or simultaneous countershock capability into a multimodal automatic system.

In coordination with providing a countershock or pacing instruction to the pacer 102, a controller 101 can also activate selective additional subsystems that can adjunctively improve upon the pacing. These additional adjunctive subsystems can include any of the subsystems described herein, including pneumatic, mechanical, acoustical, or other subsystems, to enhance countershock or pacing efficacy. The controller 101 can provide instructions to the pacer(s) 102 to provide electrical countershock that may be single, dual simultaneous/sequential, or N simultaneous/sequential, which can be delivered via two or more simultaneous/sequential electrode pairs. One of the electrode pairs may include a positive or negative electrode within the esophagus of the patient. In various embodiments, the CETEES can have one pair of countershock electrodes 302, or can have more than two countershock electrodes, and in various embodiments the CETEES can have four or more countershock electrodes. In various embodiments, the CETEES can have a pair of electrodes that can be positioned to apply posterior-anterior countershocks.

Contact Force Enhancement Subsystem

As discussed above, pushing on classic defibrillation paddles or modern self-adhesive electrode pads: 1) increases electrode contact pressure, 2) lowers thoracic resistance, 3) increases current flow, and 4) enhances the efficacy of countershock. But these salutary mechanical interventions are never used clinically because there previously existed no safe method or device to push on self-adhesive electrode pads at the moment of electrical discharge.

Similar adjunctive enhancements to efficacy can occur if the electrodes 302 used for myocardial capture during transthoracic cardiac pacing are also pushed on at the moment of each electrical discharge. Specifically, the countershock or pacing electrodes 302 may have contact force enhancers 107, such as pneumatic bladders 303, mechanical actuators 307, and/or circumferential constrictors 306 behind them to provide force on the electrodes.

The contact pressure enhancing subsystem 107 to enhance contact pressure, i.e. applying force to the pads or paddles, may have one or more mechanisms for applying force.

These mechanisms for applying force can include one or more of: 1) a selective pneumatic bladders 303, and/or mechanical actuators 307 that push on gel electrode pads 302, 2) a circumferential constriction pneumatic bladder 306 that pushes on all electrode pads 302 at the moment of electrical discharge or 3) a combination of those mechanisms. In various embodiments, selective or full circumferential enhancement of contact force pressure may be achieved by mechanical means such as screws or piston mechanisms. Optimization of contact pressure in electrical countershock or pacing as monotherapy for dysrhythmias has found that at least 50 Newtons of force may be needed to achieve enhanced current flow. In various embodiments, the controller can begin with at least 90 Newtons of force being applied a priori at the beginning of treatment, and in various embodiments, the controller can adapt the force in response to inputs such as sensed biomarkers and subsystem feedback to optimize the treatment for each individual patient. Generally, the force applied would be below the thresholds associated with skeletal or visceral organ injury.

Figure 4:
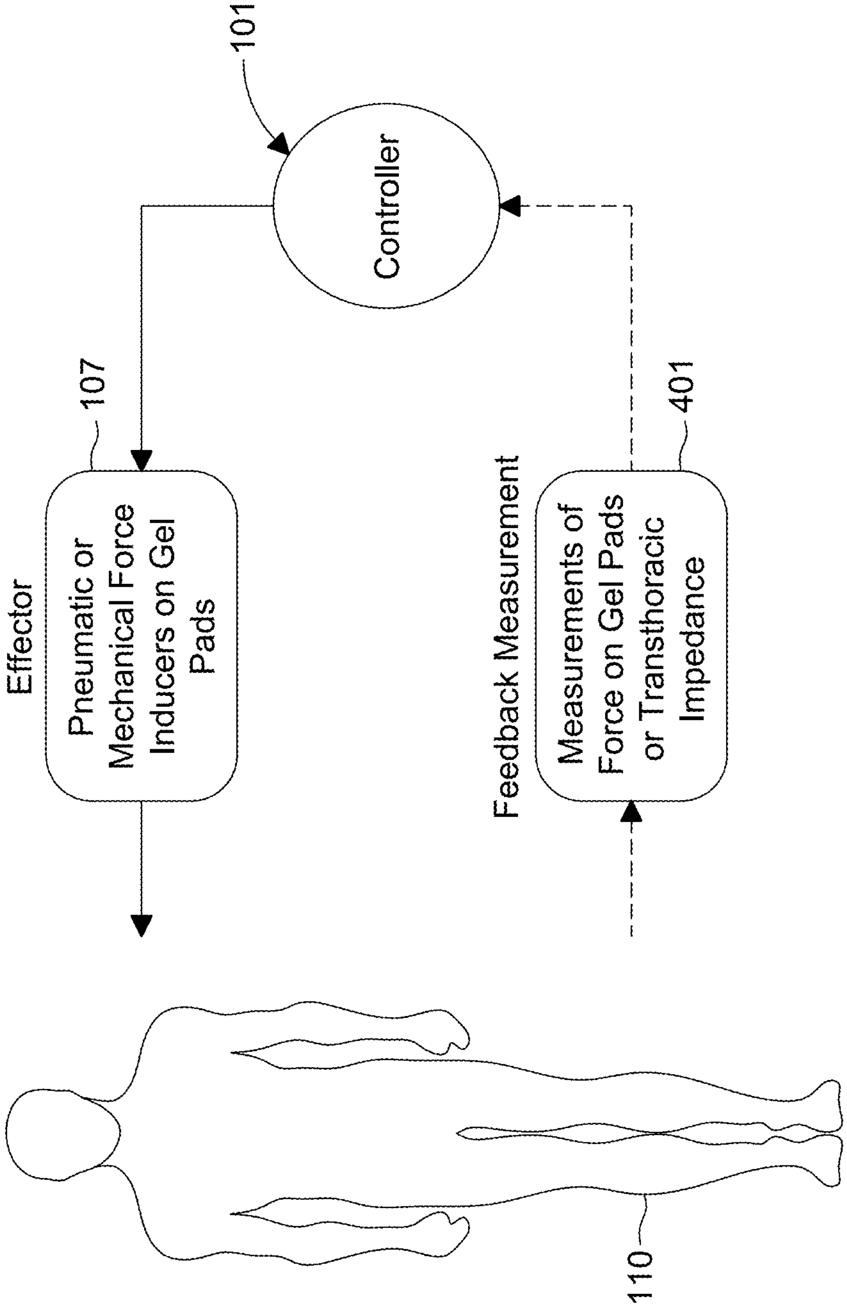
FIG. 4 is a schematic diagram of a feedback and optimization loop for an electrode contact pressure enhancer subsystem, according to an illustrative embodiment.

FIG. 4 is a schematic of the contact pressure enhancer subsystem including the feedback mechanisms 401 and effector mechanisms 107 along with the controller 101.

Various Subsystems for Altering Ventilatory Status

As discussed above, air acts as an insulator that impairs current flow. In the human thorax, the lungs act as air based insulators. There is a strong relationship between the phase of ventilation and the transthoracic resistance. The circumferential constrictors and/or electrode contact force enhancers of the CETEES may alter the ventilatory state of the lungs at, just before, or throughout the moment of electrical discharge so as to lower transthoracic resistance. More specifically, one or more of the various subsystems for altering ventilator status can force exhalation and minimize the diameter of the thorax by placing the lungs at maximal expiration at the time of countershock or pacing electrical discharge.

This may be achieved by a number of means:

- Inflation of a circumferential or partial circumferential constriction pneumatic bladder or band.
- Constriction of a circumferential belt or partial circumferential belt by mechanical means such as screws or piston mechanisms.
- Transcutaneous functional electrical stimulation (FES) so as to cause one or more respiratory muscles to contract, including FES of the rectus abdominis, which acts to assist exhalation.
- If the patient is undergoing assisted ventilation, the controller can synchronize ventilation with electrical discharge of the pacer so as to apply electric current at or near full exhalation. In various embodiments, the pattern of synchronized ventilation can be adjusted so as to optimize one or more of thoracic resistance, capacitance, impedance, and/or current flow.

Figure 5:
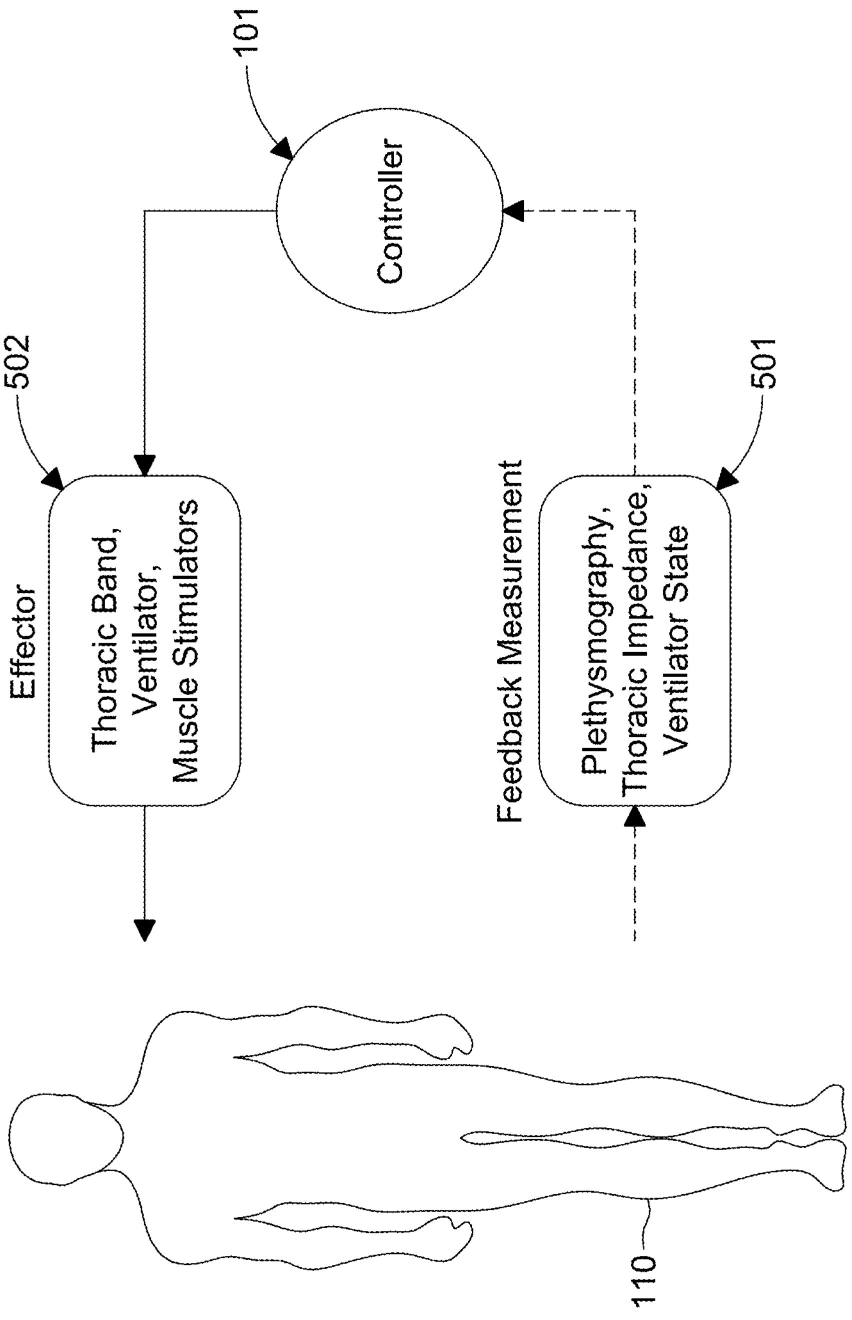
FIG. 5 is a schematic diagram of a feedback and optimization loop for a ventilation subsystem, according to an illustrative embodiment.

FIG. 5 is a schematic of the ventilation at exhalation subsystems including the feedback mechanisms 501 and effector mechanisms 502 along with the controller 101. For the purposes of this device it may be sufficient to be near maximal exhalation, which is traditionally called residual volume, such a value being defined as within 20 percent of a patient's residual volume.

Acoustic or Vibratory Force Subsystem

Turning back to FIGS. 1-3, acoustic, ultrasound or vibratory energy can be combined adjunctively with electrical energy to more efficiently and effectively achieve cardioversion or pacing. Through the application of acoustic, ultrasound or vibratory energy, a CETEES 100 can place the myocardium 305 into a state more amenable to cardioversion or pacing. For the purposes of describing this device or method it should be assumed that whenever acoustic, ultrasound or vibratory energy are referred to the other energy frequencies are included.

The application of acoustic, ultrasound or vibratory energy can have a salutary effect on electrophysiologic characteristics of the myocardial substrate that is initiating or maintaining the dysrhythmia. While inefficient as a sole treatment of dysrhythmias, acoustic, ultrasound or vibratory energy can be useful as an adjunct to enhance the efficacy of electrical cardioversion or pacing when combined with other adjunctive techniques. With respect to countershock, the acoustic, ultrasound or vibratory energy may be applied to the myocardium 305: 1) for a period of time before electrical countershock, 2) coincident with electrical countershock, 3) after electrical countershock, 4) a combination of these phases. Application of the acoustic, ultrasound or vibratory energy before countershock can place the myocardium in condition for the countershock to be more effective.

The use of acoustic, ultrasound or vibratory energy as an adjunctive intervention can be associated with optimal parameters. In various embodiments, the controller can begin with acoustic, ultrasound or vibratory energy being applied a priori at the beginning of treatment, and in various embodiments, the controller can adapt the acoustic, ultrasound or vibratory energy in response to inputs such as sensed biomarkers and subsystem feedback to optimize the treatment for each individual patient.

Figure 6:
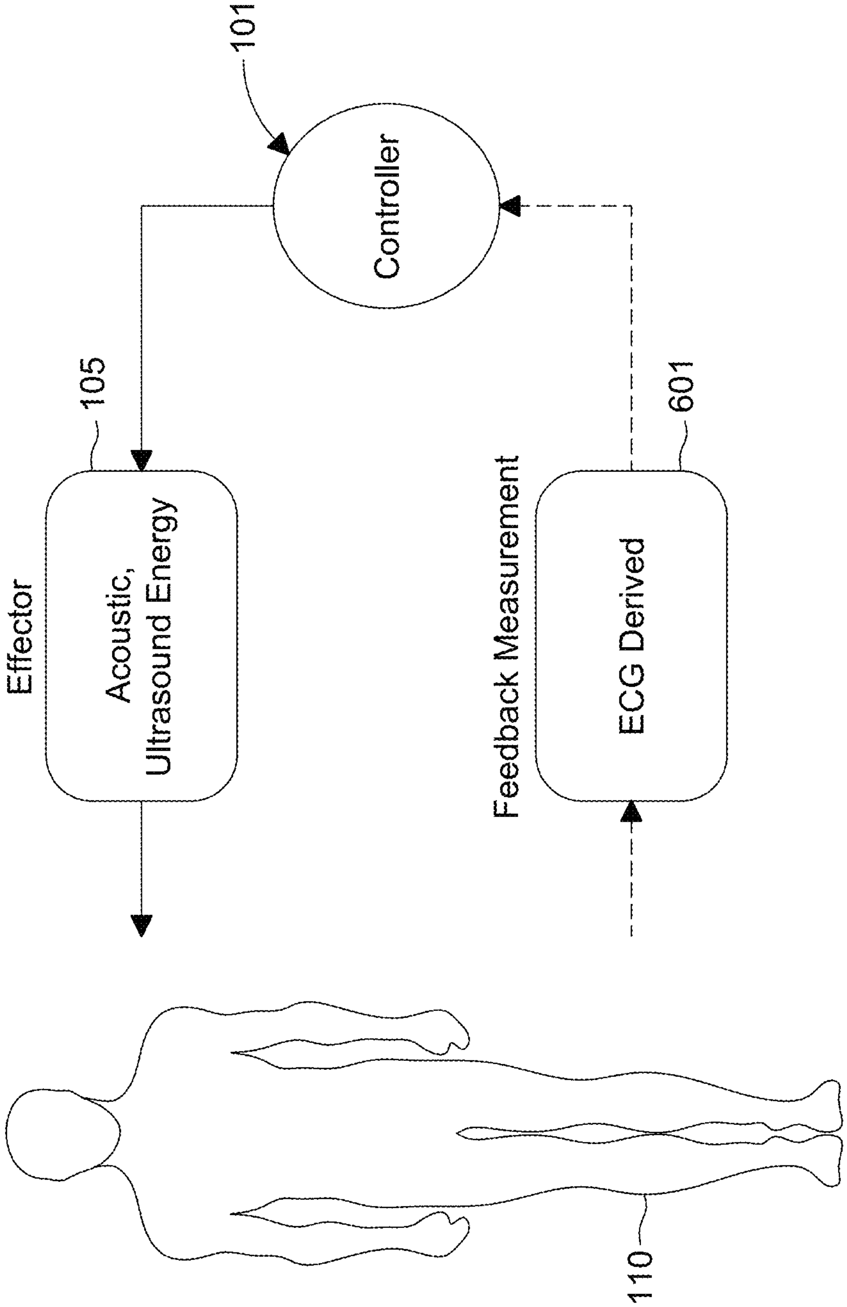
FIG. 6 is a schematic diagram of a feedback and optimization loop for an acoustic/ultrasound subsystem, according to an illustrative embodiment.

FIG. 6 is a schematic of the cardiac acoustic subsystems including the feedback measurement and effector mechanisms 103 along with the controller 101.

VAGAL NERVE STIMULATION SUBSYSTEM

Turning back to FIGS. 1-3, separately or in combination with other interventions, a CETEES may additionally place the myocardium 305 into a state more amenable to cardioversion or pacing by means of vagal nerve stimulation. Application of this stimulation may be used adjunctively to enhance to probability of acute electrical cardioversion of atrial fibrillation or similarly as an assist in transthoracic pacing. With respect to vagal nerve stimulation energy may begin to be applied: 1) for a period of time before electrical countershock, 2) coincident with electrical countershock, 3) after electrical countershock, 4) a combination of these phases. Because the effect of vagal nerve stimulation likely takes time intervals on the order of minutes to affect the electrophysiologic state of the myocardium 305, the controller can synchronize the vagal stimulation to begin 5 to 10 minutes before countershock or pacing.

Figure 7:
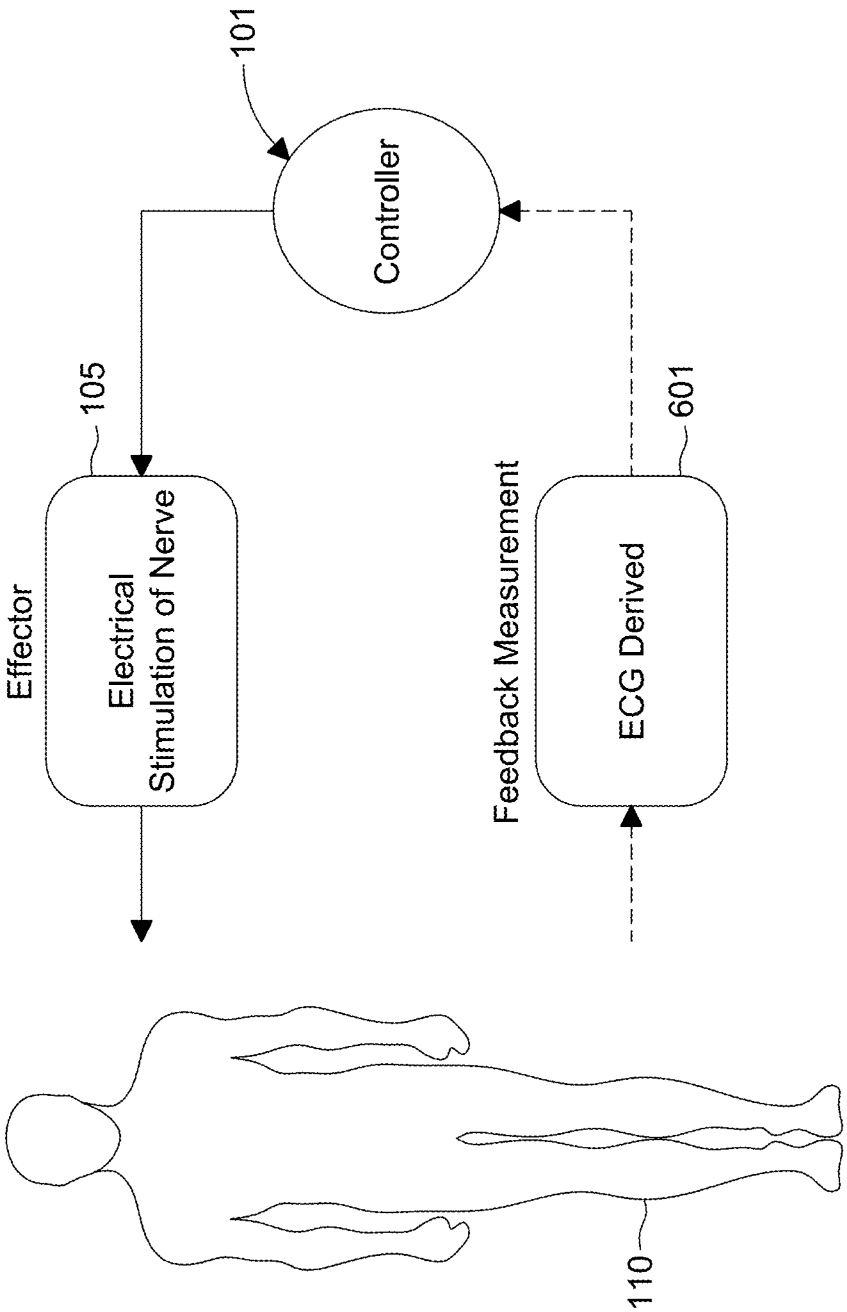
FIG. 7 is a schematic diagram of a feedback and optimization loop for a cardiac vagal stimulation subsystem, according to an illustrative embodiment.

FIG. 7 is a schematic view of the vagal stimulation subsystem including the feedback measurements and effector mechanisms 105 along with the controller 101.

Biomarker Inputs

Turning back to FIGS. 1-3, the CETEES can have a controller 101 that can input biomarker inputs and inputs from various subsystems, and can coordinate the electrical discharge in response to these inputs. Biomarkers inputs may include but not limited to: ECG, ventilatory status, impedance measurements, and ventilatory gas measurements, among others.

The electrical system for the countershock circuitry may measure one or more of: thoracic resistance, capacitance, impedance, or current flow. In various embodiments, the controller can receive biomarker inputs from various afferent sensors provided at locations around the patient for collecting biomarker data. The controller can also receive status update from one or more of the effector subsystems. Such a control system could allow electrical countershock optimized by the measurement of one or more of thoracic resistance, capacitance, impedance, or current flow; electrical countershock at the optimal portion of the ventilatory cycle; optimization of the electrical countershock by applying current through a selected subset of the patient-facing electrodes; adjustment of the force, location or timing parameters of chest constriction so as to optimize one or more of thoracic resistance, capacitance, impedance, or current flow; and/or adjustment of the parameters of synchronized ventilation so as to optimize one or more of thoracic resistance, capacitance, impedance, or current flow. The controller can optimize the relationships in response to various inputs.

Optimization of Subsystems

Each subsystem's energy characteristics can be pre-set at a priori optima, and/or can be optimized in real-time based on acquired inputs including tissue and organ status.

In various embodiments, the subsystem energies or frequencies may be varied while ECG parameters known to be associated with, and likely predictive of, successful countershock or pacing (i.e. Zeemering et al discussed above) are measured. These methods can include optimization through closed-loop control. Once the optima are achieved, countershock current can be applied. In the case of cardiac pacing, capture of the myocardium 305 may be attempted at the same time that the optimization of the subsystem(s) is occurring.

And additionally, the subsystem energies or frequencies may be varied while the value of one or more previously determined synthetic machine learning derived algorithms or equations are measured. Once the optimal or near-optimal values are achieved, countershock current can be applied. In the case of cardiac pacing, capture of the myocardium 305 may be attempted at the same time that the optimization of the subsystem, based on the machine learning derived equation, is occurring.

The measurements of the ECG can be useful and readily available in patients suffering cardiac rhythm disorders. By way of non-limiting example, the ECG QRS rate, QRS rate spectroscopy, and atrial fibrillation waveform spectroscopy can be indicative of the state of the myocardium 305 and likely predictive of dysrhythmia termination or myocardial pacing capture.

Control Systems

In various embodiments, the processor controlling the cardioversion or pacing can apply the current for electrical countershock to differing combinations of electrodes 302 such that multiple paths across the chest can be utilized simultaneously or in sequence. In various embodiments, the processor controlling the timing can apply the current for electrical cardioversion or pacing to combinations of electrodes so that two countershocks at an angle to one another can be applied simultaneously. In various embodiments, the processor controlling the cardioversion or pacing can apply the current for electrical countershock to a series of electrodes such that the pathway of current flow through the chest can start in one or more directions and can transition into a different set of directions. In various embodiments, the mechanical, pneumatic, or hydraulic components can vary the force or pattern of chest compression or constriction so as to enhance the efficacy of cardioversion or pacing. In various embodiments, the processor can receive measurement data from one or more of thoracic resistance, capacitance, impedance, and/or current flow, and can adapt treatment in real time in response to measured data to provide customized treatment to individual patients.

Synchronization of Components

The device described herein can adjunctively enhance the efficacy of electrical countershock or pacing by means of enhancing current flow and or altering the myocardial substrate. Depending on the specific adjunctive subsystem or subsystems, the temporal relationships, also referred to as the synchronizations, between current flow and the activation of various adjunctive subsystems may be different.

By means of a non-limiting example, these synchronizations may be in the range of:

- For the subsystem that increases contact pressure of the self-adhesive gel electrode pads, optimal synchronizations may be simultaneous with electrical discharge, or from just before to just after electrical discharge. Contact pressure can be at an increased state during electrical discharge.
- For the subsystem(s) that force exhalation and minimize the diameter of the thorax by placing the lungs at maximal expiration, optimal synchronization may start at least from approximately 20% of the respiratory cycle length before electrical discharge through completion of electrical discharge. This can allow adequate time for movement of the anatomic chest structures.
- For the subsystem that emits acoustical or vibratory energy toward the myocardium 305, the longest possible period of application may enhance the effect. For electrical countershock of a dysrhythmia, the acoustic, ultrasound or vibratory energy might initiate as soon as possible after application of the device, but at a minimum at least seconds before electrical discharge and end coincident with termination of electrical discharge.
- For enhancement of transthoracic pacing, the subsystem that emits acoustical or vibratory energy toward the myocardium 305 the transmitted continuously during pacing or coincident with each electrical discharge.
- For the subsystem that emits electromagnetic or acoustical energy to the vagus nerve, the longest possible period of application may enhance the effect. For electrical countershock of a dysrhythmia, the acoustic, ultrasound or vibratory energy directed at the vagus nerve might initiate as soon as possible after application of the device, but at a minimum at least seconds before electrical discharge and end coincident with termination of electrical discharge.
- For enhancement of transthoracic pacing, the subsystem that emits electromagnetic or acoustical energy to the vagus nerve might transmit continuously during pacing or coincident with each electrical discharge.

Component Physical Ingegration in various embodiments, the patient-facing components for electrical countershock, such as adhesive gel electrodes 302, and the associated electronics such as the processor may be fully incorporated into the housing of an automated mechanical/pneumatic CETEES system. In various embodiments, one or more of the subsystems may be housed separately from the main device. In the case of the countershock subsystem, it may be housed separately and connected to the main device by electrical cables. A system integrating multiple hemodynamic enhancements with cardioversion or pacing may, at any given moment, only be applying a subset of its multiple modalities.

For ease of use, many—if not all—components and subsystems applied to the patient thorax may be preinstalled within an inelastic outer shell 301 capable of being placed circumferentially around the thorax at the level of the myocardium 305. This shell may be made of various fabric materials and incorporate a closure mechanism allowing appropriate sizing. This shell allows subsystems applying mechanical, acoustical, and electrical forces to have a physical structure to maintain optimal configuration and apply Newtonian counterforce against.

Non-limiting Example, an Embodiment

By way of non-limiting example, an embodiment can include a fully integrated electromechanical or electropneumatic CETEES system that can include one or more of the following components:

- A controller 101 capable of controlling each subsystem based on the biomarker feedback and system status measurements. The control subsystem can execute precision adaptive sequences targeted toward pre-determined optima.
- Countershock or pacing subsystem 102.
- Connection to the patient ventilator 104.
- Connection to the patient monitor system capable of acquiring patient measurements 106 such as the electrocardiogram and photoplethysmogram.
- A non-elastic outer shell 201 that contains and maintains the location and orientation of the patient facing subsystems. This shell also provides a structure against which subsystems may push so as to allow counterforce to be directed inward toward the patient. This shell may be vest-like in shape and adjustable for patients of varying size and circumference. The circumferential constriction mechanism may be part of the non-elastic outer shell 201 or applied to the non-elastic outer shell.
- electrode pads 302.
- Contact force enhancers 107. Contact force enhancers 107 can include one or more of bladders 303, electromechanical pushing mechanisms 307, and/or circumferential constrictor(s) 306. A fully circumferential or partially circumferential exhalation constrictor 108 to force exhalation and minimize the diameter of the thorax. This exhalation constrictor 108 may be just inside of the non-elastic outer shell 201.
- Acoustic or vibratory emitters 304 capable of transmitting acoustical or vibratory energy to the myocardium 305. By way of non-limiting example, this can be an ultrasound emitter.
- A vagus nerve stimulator 105 capable of transmitting electromagnetic or acoustical energy to the vagus nerve.
- A muscle electrical stimulator 109 capable of transcutaneous muscle stimulation.
- Various sensors 206 that can include sensors for measuring biomarkers such as ECG, ECG derived biomarkers such as Fourier transform based power spectra, ET-$CO_2$, indicators of tissue oxygenation or energetics (i.e. NIRS), indicators of hemodynamics such as photoplethysmography, vital signs, and/or measures of ventilatory status.
- A TCP subsystem 102 that can be controlled by the controller 101 so that the TCP subsystem can provide countershocks or pacemaker beats in either a standard or sequential pattern.
- A fully circumferential exhalation band to force exhalation and minimize the diameter of the thorax 109. The exhalation band may be just inside of the non-elastic outer shell 301.
- Biomarker subsystems capable of measuring patient or organ status. One or more biomarker or system status input subsystems chosen from a group including: ECG, ECG derived biomarkers such as fast-Fourier transform based power spectra, ET-$CO_2$, indicators of tissue oxygenation or energetics (i.e. NIRS), indicators of hemodynamics such as photoplethysmography, among others.
- Electrode contact pressure enhancer subsystem(s) 107 capable of pneumatically and/or mechanically applying pressure to the electrodes. In various embodiments the electrodes can be combined with one or more contact pressure enhancer subsystems(s) 107. The contact pressure enhancer subsystem(s) can selectively increase electrode contact pressure.

The countershock/pacemaker subsystem 102 and its associated electronics may be physically integrated into the device, or it can be separate, with or without monitor, connected to the controller wirelessly or by a cable. In various embodiments, the electrical countershock electrodes 302 can be physically integrated into patient-facing portions of other subsystems, including, for example, the thoracic circumferential constrictor sub system 306.

Multiple TCP electrodes 302 can be used to create multiple transthoracic pathways through the patient 110. Electric current can be directed through selected countershock electrodes 302 to create various transthoracic pathways through the patient 110. Countershock or pacing may be improved by application of multiple transthoracic pathways that are electrified near simultaneously or sequentially. Incorporation of the TCP electrodes 302 into patient facing surfaces of the device allows for multiple electrodes to be discharged simultaneously or sequentially, and allows for the use of one or more transthoracic pathways between various electrodes. In some cases, an anterior-posterior transthoracic pathway may be optimal. The potentially optimal anterior-posterior electrode placement and current path may be utilized singly, or as part of a multi-shock simultaneous or sequential pattern. Incorporation of the TCP electrodes into the body of the CETEES device allows for fast and easy placement of electrodes in various locations around the patient, including the anterior and posterior of the thorax.

A CETEES can be controlled by a controller, or processor, 101 that can include, or be connected to, a plurality of modules, data inputs, and control outputs, and a user interface. The processor can be contained within a general purpose, or a dedicated, computing device, such as a PC, laptop, tablet, or smartphone. In various embodiments, the controller 101 can be built into, or incorporated within, the housing of the CETEES. The computing device can include a user interface that can be a keyboard, mouse, touch screen or similar device, and a display that can include a graphic user interface screen. In practice, a user can input instructions for a procedure through the user interface into the processor. The modules and/or submodules of the processor can then process the instructions, collect measurements, and provide information and/or instructions to the various subsystems of the CETEES.

Prior to delivering a countershock instruction, the controller 101 can activate selective pneumatic or mechanical adjuncts, described above, to increase electrode contact pressure. The controller 101 can then provide electrical countershock that may be single, dual simultaneous/sequential, or N simultaneous/sequential, which can be two or more simultaneous/sequential countershocks. One of the electrode pairs may include a positive or negative electrode within the esophagus.

In various embodiments, the countershock electrodes can be adhesive gel electrodes that can be a disposable component that is pre-manufactured so as to be easily inserted into or removed from the patient-facing mechanical or pneumatic components.

By way of non-limiting example, an illustrative embodiment of a CETEES can integrate standard self-adhesive gel electrode pads with one or more additional subsystems. The additional subsystems can be adjunctive to the countershock treatment. These additional subsystems may achieve:

- Increased contact pressure, i.e. applying force to the pads or paddles to press them against the patient;
- Synchronization with ventilation, i.e. applying the current at an optimal phase of the ventilatory cycle. Specifically, application of the transthoracic cardioversion, or pacing electrical current at or near the time of maximum ventilatory exhalation;
- Altering the anatomic shape of the thorax to minimize resistance to current flow across the myocardium. For instance, decreasing the anterior to posterior dimension of the chest;
- Placing the myocardium into a state more amenable to cardioversion or pacing by means of applying acoustic, ultrasound or vibratory energy; and
- Application of vagal nerve stimulation.

A CETEES may also achieve improved cardioversion or pacing by varying the combination, location, or current pathways of the electrode pads to use multiple paths across the chest. This can include applying two or more countershocks simultaneously along paths that are at an angle to each other. In various embodiments, two counter shocks can be delivered simultaneously along paths that can be at a 90° angle to one another and/or applying multiple countershocks at different angles relative to each other in succession.

In various embodiments, a CETEES can be: 1) adjunctive in application of multiple subsystems, 2) automated, 3) integrated, 4) computer controlled, 5) electromechanical, 6) electrophysiologic 7) optimized, and/or 8) controlled through closed-loop feedback.

Subsystems Adjunctive to Countershock or Pacing

A CETEES can include devices or subsystems that provide countershock or transthoracic pacing, and in various embodiments, a CETEES may be distinct from separate devices that provide transthoracic cardioversion or pacing and be connected to them via a controller 101. Such separate devices are common clinically. A CETEES can include an integrated countershock cardioverter and/or transthoracic pacemaker. The countershock cardioverter and/or transthoracic pacemaker can be a single device that can perform both functions, or the countershock and/or transthoracic pacemaker can be distinct devices. In the interest of brevity, as used herein, the terms countershock, cardioverter, countershock cardioverter, and pacemaker may be used interchangeably, and the use of a single term may include each term. In various embodiments, a CETEES may have one or more subsystems that can include: a cardioverter, a transthoracic pacemaker, contact force enhancement subsystem, an acoustic, ultrasound or vibratory energy generator subsystem, a ventilatory subsystem, a vagal nerve simulator subsystem, a controller, and/or an inelastic outer band or outer shell. The efficacy of the countershock cardioverter and/or transthoracic pacemaker functions can be adjunctively enhanced by one or more of the other subsystems including: the contact force enhancer subsystem, the acoustic, ultrasound or vibratory energy emitter subsystem, the ventilator subsystem, and/or the vagal nerve simulator subsystem. Various examples of subsystems, including the transthoracic countershock cardioverter subsystem and the subsystems that can be used to adjunctively enhance the transthoracic cardioverter functions of the CETEES are described below.

Countershock System Subsystem

As described herein, the term countershock subsystem can have an expanded spectrum of capabilities. The countershock system can do more than simply charge the electrodes and release current from the storage capacitors. It can further interface with the control processor, provide status data to the controller, and receiving instructions from the controller. In various embodiments, it can countershock via multiple positive-negative electrode pairs.

In various embodiments, a CETEES can control the combinations of electrode pads that are electrically discharged by the cardioverter such that that current is released from one or more combinations of electrode pads, so that the CETEES can utilize multiple paths across the chest. Multiple electrode pads can be used to create multiple transthoracic pathways through the patient. The use of multiple paths can include applying two or more counter shocks simultaneously along paths that are at an angle to each other. In various embodiments, two counter shocks can be delivered simultaneously along paths that can be at a 90° angle to one another. Electric current can be directed through selected countershock electrodes to create various transthoracic pathways through the patient. The electrodes used for each shock can be selected by the controller.

In conjunction with countershock, a controller can activate selected pneumatic, mechanical, acoustical, or other subsystems, as described herein, to enhance countershock or pacing efficacy. The controller can provide electrical countershock that may be single, dual simultaneous/sequential, or N simultaneous/sequential, which can include two or more simultaneous/sequential electrode pairs. In various embodiments, one of the electrode pairs may include a positive or negative electrode within the esophagus of the patient. In various embodiments, the CETEES can have one pair of countershock electrodes, or can have more than two countershock electrodes, and in various embodiments the CETEES can have four or more countershock electrodes. In various embodiments, the CETEES can have a pair of electrodes positioned to apply posterior-anterior countershocks.

Electrode Contact Force Enhancement Subsystem

As discussed above, pushing on classic defibrillation paddles or modern electrode pads can increase electrode contact pressure, which can lower thoracic resistance and increase current flow. Lowering thoracic resistance and/or improving current flow can enhance the efficacy of countershock. But these salutary mechanical interventions have not been used clinically in the past because there previously existed no safe method or device to push on self-adhesive electrode pads at the moment of electrical discharge.

In the case of a CETEES, adjunctive enhancements to efficacy can occur if the electrodes used for myocardial capture during transthoracic cardiac pacing are pushed on at the moment of each electrical discharge. As shown in FIG. 3, countershock electrodes can have electrode contact enhancers behind them to provide force on the electrodes.

For the CETEES electrode contact force enhancement system to enhance contact pressure, it may have one or more mechanisms that can apply force to the pads or paddles. These mechanisms to apply force can include, but are not limited to, electrode contact enhancing inflatable bladders 303, mechanical actuators 307, and/or circumferential constrictors 306. These systems can apply force to an electrode 302 to push the electrode against the patient 110 and/or apply force to the patient to push the patient against the electrode. In various embodiments, electrode contract force can be enhanced by a circumferential constrictor subsystem 306 that can include a pneumatic or hydraulic bladder, a series of bladders, and/or a constricting band to push on electrode pads at the moment of electrical discharge. Various combinations of those mechanisms can also be incorporated together. In various embodiments, selective or full circumferential enhancement of contact force pressure may be achieved by pneumatic or hydraulic means, and/or by mechanical means such as screws or piston mechanisms. At least 50 Newtons of force may be needed to achieve enhanced current flow, however, the contact pressure for electrical countershock pacing for dysrhythmias can be optimized for each patient, as explained more fully below.

Acoustic, Ultrasound or Vibratory Force

Acoustic, ultrasound or vibratory energy can be applied adjunctively in combination with electrical energy to more efficiently and effectively achieve countershock or pacing. This energy can be applied transcutaneously from skin surface based acoustical or vibratory emitters 304. In various embodiments, the acoustic, ultrasound or vibratory emitters 304 can be crystal or semiconductor arrays. Applying acoustic and/or vibrational energy to the patient 110 can place the myocardium 305 into a state more amenable to cardioversion or pacing.

Acoustic or vibratory energy can have at least a salutary effect on electrophysiologic characteristics of the myocardial substrate that is initiating or maintaining the dysrhythmia, and acoustic, ultrasound or vibratory energy alone can sometimes pace the myocardium 305. While often inefficient alone as a sole treatment of dysrhythmias, acoustic, ultrasound or vibratory energy can be useful as an adjunct to enhance the efficacy of electrical cardioversion or pacing. With respect to countershock, the acoustic, ultrasound or vibratory energy may be applied to the myocardium: 1) for a period of time before electrical countershock, 2) coincident with electrical countershock, 3) after electrical countershock, and/or 4) a combination of these phases. The use of acoustic, ultrasound or vibratory energy as an adjunctive intervention can be optimized for each patient. Application of acoustic, ultrasound or vibratory energy may be continuous or pulsed during pacing or continuous for a period of time before countershock.

Ventilation System

As discussed above, air acts as an insulator that impairs current flow. In the human thorax, the lungs can act as air-based insulators during countershock. There is a strong relationship between the phase of ventilation and the transthoracic resistance. The circumferential constriction mechanisms or electrode contact force enhancers of the CETEES may alter the ventilatory state of the lungs at, just before, or throughout the moment of electrical discharge so as to lower transthoracic resistance. More specifically, this subsystem can force exhalation, minimize lung volume, and minimize the diameter of the thorax by placing the lungs in a state of maximal expiration at the time of countershock or pacing electrical discharge.

Incorporation of electrodes into the patient facing surface of a circumferential constrictor can allow both enhanced electrode contact pressure and ventilatory end-exhalation for improved transthoracic resistance and countershock success. In various embodiments, a single circumferential constrictor can provide the enhanced contact pressure and the exhalation constriction.

Lung volume minimizers can also include transcutaneous Functional Electrical Stimulation (FES) which can cause one or more respiratory muscles to contract, as described in U.S. Patent Application Publication No. 2002/0128686 titled ABDOMINAL BELT WITH ADJUSTABLE ELECTRODES, the entire disclosure of which is incorporated herein by reference. In various embodiments, FES of the rectus abdominis can act to assist exhalation. If a patient is having their breathing assisted by a ventilator, the ventilator can also act as a lung volume minimizer. The ventilation can be synchronized with the countershocks to deliver countershocks during a period of minimum lung volume. Synchronization of the ventilator and the countershocks can include delivering countershocks during the optimal expiratory phase of ventilation, at the moment in a ventilation cycle when the lung volume is at a minimum. Synchronization of the ventilator and the countershocks can include delivering countershocks at the moment before forced inspiration. Synchronization of the vent ilator and countershocks can also include delaying forced inspiration until after the countershock. Maximal exhalation may be achieved by one or multiple means.

Vagal Nerve Stimulation Subsystem

Separately or in combination with other interventions, a CETEES device may place the myocardium into a state more amenable to cardioversion or pacing by means of vagal stimulation. Application of electrical vagal nerve stimulation may help to suppress episodes of paroxysmal atrial fibrillation. Adjunctive application of vagal nerve stimulation may be used to increase the likelihood of successful electrical cardioversion of atrial fibrillation and/or to increase the efficacy of transthoracic pacing. With respect to vagal nerve stimulation energy may begin to be applied: 1) for a period of time before electrical countershock, 2) coincident with electrical countershock, 3) after electrical countershock, 4) a combination of these phases. Because the effect of vagal nerve stimulation likely takes time intervals on the order of minutes to affect the electrophysiologic state of the myocardium, the synchronization relationship that is likely most effective would be for vagal stimulation to initiate 5 to 10 minutes for countershock or pacing.

Sequencing of Subsystems

Figure 9:
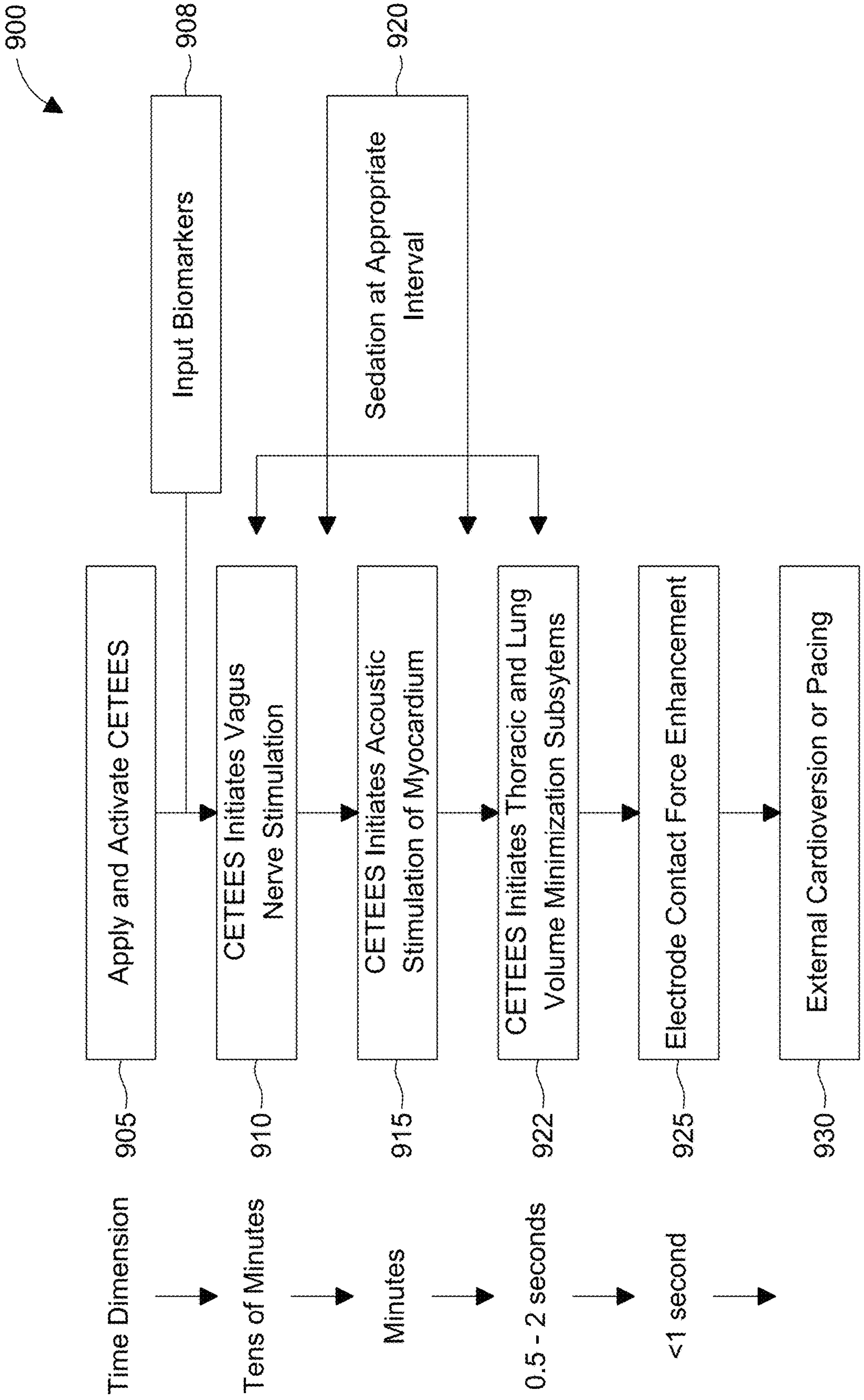
FIG. 9 is a flow diagram of an exemplary clinical process for treatment using a CETEES, according to an illustrative embodiment.

The different subsystems have differing time course kinetics for their salutary effect on countershock and pacing thresholds. Vagal nerve stimulation affects the myocardium on a timeframe of tens of minutes. Acoustical or vibratory energy likely affects the myocardium on a timeframe of seconds to minutes. Alteration in thoracic and lung anatomy so as to achieve minimized lung and transthoracic volumes requires 2 to 3 seconds to be achieved. Application of contact force to the electrodes affects transthoracic resistance-impedance on a time of milliseconds. FIG. 9 is a flow diagram of an exemplary clinical process 900 for treatment using a CETEES, according to an illustrative embodiment. By way of non-limiting example, applying the above time course kinetics, the method or device may utilize the following sequence:

At box 905, the device can be applied to the patient's chest.

At box 908, various biomarkers can be collected from the patient and provided as an input to the controller of the CETEES. An operator provide input to the CETEES confirming the intention to perform cardioversion or pacing, and a desired time to intervention.

At box 910, the vagal nerve stimulation subsystem can apply vagal nerve stimulation, and the vagal nerve stimulation can be maintained through completion of countershock or pacing. At least 10 minutes of vagal stimulation may be considered optimal.

At box 915, the acoustical or vibratory subsystem initiates application of acoustical or vibratory energy to the myocardium five to 10 minutes before cardioversion or pacing. Acoustical or vibratory energy application can be maintained through completion of countershock or pacing.

At box 920, a sedative can be administered to the patient. Depending on the sedative selected by the clinicians, the drug is administered at the appropriate interval before countershock or pacing. After drug administration, an operator input can confirm that patient sedation has been achieved.

At box 922, the thoracic constriction subsystem, the ventilator control mechanism, and/or the muscle stimulation for exhalation subsystem are activated and synchronized 2 to 3 seconds before countershock. Thoracic constriction, ventilator exhalation, and muscle stimulation for exhalation, can be maintained through completion of countershock.

At box 925, the electrode contact force enhancement subsystem applies force 100-500 ms before countershock or pacing and maintains this force through each countershock or pace.

At box 930, when the control subsystem confirms that all countershock or pacing enhancements subsystems have activated and achieved optimal parameters based on input measurements, countershock or pacing electrical discharge is applied transthoracicly.

If successful cardioversion or pacing capture is detected by measurement or operator input, the control system discontinues subsystem activation. In the case of cardiac pacing there is a cyclical reactivation sequence.

Sequence of Therapies when A CETEES is Used as an Adjunct to Cardiac Pacing

For external transthoracic cardiac pacing to be effective, the pacer must capture the myocardium electrophysiologically with each desired heartbeat. A CETEES is potentially a useful adjunct in enhancing the likelihood of initial and continued pacemaker capture of the myocardium. However, the overall configuration and the specific parameters of the subsystem will likely be different when a CETEES is used for cardiac pacing in comparison to one-time cardioversion.

Unlike termination and cardioversion of cardiac dysrhythmias, the adjunctive enhancement of pacemaker electrical capture should be maintained, and some components cycled with respect to each induced cardiac contraction. In various embodiments, the vagus nerve stimulation and acoustic enhancement may be maintained throughout the time that transthoracic cardiac pacing is being utilized.

Electrode contact force enhancement, however, may have multiple modes. In one mode, the contact force enhancement may be maintained continuously. In another mode, it may be cycled with each cardiac beat. Because this is going to be applied for periods of time longer than required for one-time cardioversion, it is possible that the force applied will be less. Transthoracic cardiac pacing is often uncomfortable for patients, requiring sedation. In various embodiments, electrode contact force enhancement may, either continuous or cycles, be increased if sedation is used.

In most cases, subsystems to induce exhalation and transthoracic minimization will not be utilized during transthoracic pacing. The standard heart rate utilized is 80 bpm. Applying exhalation or transthoracic minimization at 80 bpm would significantly interfere with ventilation and respiration.

Biomarker Inputs to the Control System

Various patient biomarkers can be measured and used to improve the efficacy of treatment in real time. Patient biomarkers can be used to improve the efficacy of countershock pacing, and patient biomarkers can be used to synchronize, coordinate, and/or optimize each of the different adjunctive treatment modalities. The CETEES can have a controller unit with a processor that can coordinate biomarker inputs, the subsystem activities, and the electrical discharge. Biomarkers may include but are not limited to: ECG, ventilatory status, impedance measurements, and/or ventilatory gas measurements, among others.

The electrical control system 101 for the countershock circuitry may measure one or more of: thoracic resistance, capacitance, impedance, or current flow. In various embodiments, these measurements can be collected through various afferent sensors provided at locations around the patent for collecting biomarker data, including but not limited to: ECG, force transducers, accelerometers, and/or electrodes for impedance. The electrical control system 101 can receive status updates from one or more of the effector subsystems. In various embodiments, these measurements can be collected through the countershock electrodes. Such a control system can optimize electrical countershock by adjusting the parameters of the electrical countershock based on the measurement of one or more of thoracic resistance, capacitance, impedance, or current flow. The control system can use measurements of patient breathing and the breathing cycle to coordinate electrical countershock to be delivered at the optimal portion of the ventilatory cycle.

The control system 101 can use biomarker measurements 106 such as thoracic resistance, capacitance, impedance, and/or current flow to identify the electrodes most likely to be most efficacious and optimize application of the electrical countershock by applying current through a selected subset of the patient-facing electrodes. The control system can use biomarker measurements of thoracic resistance, capacitance, impedance, and/or current flow to adjust the force, location and/or timing parameters of chest constriction so as to optimize one or more of thoracic resistance, capacitance, impedance, or current flow. Optimizing thoracic resistance, capacitance, impedance, and/or current flow can result in improved efficacy of countershock or pacing.

Optimization of Subsystems

Each subsystem's energy or force characteristics may either be pre-set at a priori optima, and/or can be optimized in real-time based on measured tissue and/or organ status. The probability for successful or failed countershock or pacing can be known at differing subsystem energies, frequencies, or forces, and the pre-set a priori optima can be the energies, frequencies, or forces known before treatment starts to be the most likely to lead to successful countershock or pacing. In various embodiments, the controller can begin treatment with pre-set a priori optima, and can then optimize in real time to improve treatment as the treatment is occurring by collecting biomarker measurements and adjusting various subsystems' energy or force characteristics in response to the collected biomarker measurements.

In various embodiments, the subsystem energies or frequencies may be varied in response to ECG parameters known to be associated with, and likely predictive of, successful countershock or pacing. Once the subsystem parameters predicted to be most effective are determined and applied, countershock or pacing current can be applied. In the case of cardiac pacing, capture of the myocardium may be attempted at the same time that the optimization of the subsystem is occurring.

In various embodiments, the subsystem parameters including but not limited to energies, frequencies and/or forces may be varied while the value of one or more previously determined synthetic machine learning derived algorithms or equations are measured. Once the optimal or near-optimal values are achieved, countershock current can be applied. In the case of cardiac pacing, capture of the myocardium may be attempted at the same time that the optimization of the subsystem, based on the machine learning derived equation, is occurring.

The measurements of the ECG are useful and readily available in patients suffering cardiac rhythm disorders. By way of non-limiting example, the ECG QRS rate, QRS rate spectroscopy, and atrial fibrillation waveform spectroscopy can be indicative of the state of the myocardium and likely predictive of dysrhythmia termination or myocardial pacing capture and can be used to improve the efficacy of both cardioversion and pacing.

In various embodiments, plateaus in measured biomarkers may be used in determining subsystem optima. As used herein, "biomarker" can include, as non-limiting examples, various measurements of the heart and heart activity, respiration, etc., and can include transthoracic impedance or other electrical measurements taken from the patient. By way of non-limiting example, a parameter of a subsystem, such as force, frequency, or energy, can be adjusted in one direction until there is no further improvement in the measured biomarker—then the force, energy or frequency may be decreased to the range around the onset of plateau and the subsystem can be considered optimized. This optimization can be performed to determine optimal settings for one or more subsystems in real time to provide the best treatment for an individual patient. Similar optimizations can be performed to determine optimal settings for various parameters including force, energy, frequency, and/or other parameters. With respect to cardiac related interventions, one or more of the ECG QRS rate, QRS rate spectroscopy, or atrial fibrillation waveform spectroscopy, can be measured as one or more subsystem settings are adjusted, and the onset of plateau identified. A synthetic multivariable equation or algorithm incorporating more than one of these measurements may be determined by techniques called machine learning and may have performance superior to any individual measurement alone. Machine learning can be performed in real time as the treatment is occurring so that one or more personalized algorithms can be created for each specific patient, thereby improving treatment for that patient.

With respect to optimization of the electrode pads contact force enhancer subsystem 107, the pneumatic or mechanical force applied to the gel electrode pads 302 could be increased while the transthoracic impedance-resistance is measured. Once the measured biomarker plateaus, that is to say, once there is no further improvement in transthoracic impedance-resistance with application of additional force, then the force is decreased to the range around the onset of plateau and the subsystem is considered optimized. In various embodiments, one or more of the ECG QRS rate, QRS rate spectroscopy, or atrial fibrillation waveform spectroscopy, can be measured and the force associated with onset of plateau of the biomarker identified. In various embodiments, this can be in combination with measurements of impedance, capacitance, or other measurements of physical characteristics. As with other subsystems, a synthetic multivariable equation or algorithm incorporating more than one of these measurements and/or other measurements described herein may be determined by techniques called machine learning and may have performance superior to any individual measurement alone. By way of non-limiting example, the time course for application of increasing force to the electrode pads by the contact force enhancer subsystem might occur during the 1 to 2 seconds before projected countershock.

Similarly, the subsystem that applies acoustic, ultrasound or vibratory energy to the myocardium may be optimized. More specifically, one or more of the ECG QRS rate, QRS rate spectroscopy, or atrial fibrillation waveform spectroscopy, can be measured while the acoustic, ultrasound or vibratory energy is increased. Once the measured biomarker plateaus, that is to say, once there is no further improvement with application of additional energy, then the energy is decreased to the range around the onset of plateau and the subsystem can be considered optimized. By way of non-limiting example, the time course for application of increasing acoustic, ultrasound or vibratory energy to the myocardium can occur during the 1 to 2 minutes before projected countershock.

Similarly, the one or more subsystems that place the lungs as close as possible to full exhalation may be optimized. More specifically, one or more of the transthoracic resistance, measured lung volume, ECG QRS rate, QRS rate spectroscopy, or atrial fibrillation waveform spectroscopy, can be measured while one or more of 1) the chest is constricted or 2) the ventilator applied relative vacuum, or 3) transcutaneous muscle stimulation is applied. Once the measured biomarker plateaus, that is to say, once there is no further improvement with application of additional exhalation, then the lung volume can be adjusted to the range around the onset of plateau and the subsystem is considered optimized. By way of non-limiting example, the time course for placing the lungs at or near full exhalation can occur during the 1 to 2 seconds before projected countershock.

Similarly, the subsystem that induces vagal nerve stimulation may be optimized. Vagal nerve stimulation generally causes the heart rate (QRS rate) to decrease, and the degree of decrease may be used as a biomarker indicator of the degree of stimulation. More specifically, one or more of the ECG QRS rate, QRS rate spectroscopy, or atrial fibrillation waveform spectroscopy, can be measured while the transcutaneous energy is increased. Once the measured biomarker plateaus, that is to say, once there is no further improvement with application of additional energy, then the energy can be decreased to the range around the onset of plateau and the subsystem can be considered optimized. By way of non-limiting example, the time course for application of vagal nerve stimulation might occur during the 1 to 5 minutes before projected countershock.

With respect to the optimization of each subsystem, a synthetic multivariable equation or algorithm incorporating more than one of these measurements may be determined by techniques called machine learning and may have performance superior to any individual measurement alone in optimization of each subsystem. In various embodiments, the optimization of multiple subsystems may occur simultaneously with alternating windows during which each subsystem is allowed to affect ECG derived biomarkers or transthoracic impedance.

Each subsystem's parameters, including but not limited to timing, energy, or force characteristics can be pre-set at predetermined values most likely to lead to the best treatment efficacy, and/or can be optimized in real-time based on measured biomarker data such as tissue and organ status. The control system can begin treatment with predetermined parameter values, and can then optimize in real time to improve treatment as the treatment is occurring by collecting biomarker measurements and adjusting various parameter values in response to the collected biomarker measurements.

In various embodiments, the subsystem parameter values, such as force, energy, and/or frequency may be varied while ECG biomarker measurements known to be associated with, and likely predictive of, successful countershock or pacing are measured.

Synthetic predictors of countershock success may be developed by machine learning. U.S. Pat. No. 9,719,842, titled METHOD FOR THE DISCOVERY, VALIDATION, AND CLINICAL APPLICATION OF MULTIPLEX BIOMARKER ALGORITHMS BASED ON OPTICAL, PHYSICAL, AND/OR ELECTROMAGNETIC PATTERNS to Paradis, the entire disclosure of which is incorporated herein by reference, describes methods for development of synthetic multivariable diagnostic and prognostic algorithms. Machine learning techniques can also be applied to data obtained during atrial fibrillation or other cardiac dysrhythmias.

Although uniplex measurement of cardiac parameters at single locations is often inadequate in the development of accurate diagnostic methods, it may be appreciated that a great deal more information is available in the anatomic and temporal patterns. Multiple sensors may be placed at physiologically distinct locations, and machine learning can be utilized to derive algorithms that may combine multiple measurements to create a synthetic biomarker that outperforms any single measurement clinically in predicting countershock success and/or indicating subsystem parameters that will increase the likelihood of countershock success.

Useful mathematical diagnostic algorithms may be developed using the in silico techniques variously called machine learning, data mining, and big data, among other terms. For the purposes of the present disclosure, the term "machine learning" will be used to represent all possible mathematical in silico techniques for creation of useful algorithms from large data sets. The term "algorithm" will be utilized in reference to the clinically useful mathematical equations or computer programs produced by the process disclosed. It should be clear that the present disclosure is not describing the application of a particular known algorithm in a clinical setting, but rather the present disclosure provides a method of developing new patient-specific algorithms, individualized for each patient, in real time for each patient as that patient is receiving treatment. This allows for the treatment efficacy to be improved as the treatment is taking place.

The performance of machine learning derived algorithms can be independent of the specific in silico software routine used for its derivation. The numerous specific in silico techniques may be categorized as supervised, unsupervised, reinforcement, and association rule learning, statistical classification, partition and hierarchical clustering, and deep learning techniques, among others. Among the most commonly used are the various forms of regression, including multiple linear and logistic regressions. If the same training data set is used, techniques as different as supervised learning, unsupervised learning, association rule learning, hierarchical clustering, multiple linear and logistic regressions are likely to produce algorithms whose clinical performance is indistinguishable or nearly indistinguishable.

Although the techniques of machine learning are to a great extent interchangeable, the independence of the individual variables used in the model is more important. Multiple variables will bring no additional diagnostic performance if they are highly correlated and essentially measure the same tissue parameter.

The probability of deriving clinically useful algorithms using the techniques of machine learning is enhanced if the number of input variables is increased and they are independent measures of pathophysiologically distinct information. Thus, the placement of sensors in a CETEES can be intended to obtain measurements in as many physiologically distinct location as possible. ECG may be measured from standardized locations and transthoracic impedance may be measured across the chest.

Some of the machine learning techniques require a classifier. An input parameter is used to modify the pre-test probability distribution of other inputs of the mathematical model, or even the final multiplex algorithm. Individual inputs to the algorithms, or pattern of multiple inputs to the algorithms, may be used in combination with any other input to create a synthetic biomarker whose diagnostic performance is superior to that of the individual inputs.

Such development processes may be iterative, and the first-pass algorithm discovery and optimization may be further optimized by inclusion of patient, clinical, hospital or epidemiology data as inputs to the machine learning process. Biomarker patterns or algorithms may be adaptive, improving over time or as a function of feedback within a specific epidemiologically useful unit. For example, the biomarker algorithm may be different in hospitals whose incidence of the disease in question are different. Some of these inputs may be adaptable at the bedside, as for instance, the patient's age or sex. Some or all of the input parameters may also be obtained internally from the patient via, for example, tomography or imaging.

Temporal patterns are the change in one or more components over time. Different temporal patterns may be used in relation to differing inputs. Temporal patterns that may be used clinically in algorithms can include one or more of: stable and unchanged, baseline to present, increasing or decreasing instability, accelerating deterioration, stabilizing deterioration, and/or improvement.

Patterns of measured biomarkers may be used in combination with non-optical data such as patient demographics, vital signs, in-vitro diagnostics, and/or any other input whose effect on the probability distribution of the likelihood of countershock success and/or probability distribution indicating subsystem parameters that will increase the likelihood of countershock success is favorable to diagnostic performance. Maximizing the efficacy of computational models may include incorporating data such as patient demographics, other vital signs, or in vitro data, among others.

In various embodiments, data collected from various sensors, also referred to as sensory signals, can be input into the processor for the purpose of optimization and/or synchronization of electrical cardioversion or pacing and various adjunctive subsystems, and may originate from one or more of: an electrocardiogram, an accelerometer, a force transducer, ET-CO2, SPO2, an acoustical microphone, and/or the mechanical or electrical subsystems. The controller 101 can input the sensory data from the various biomarker sensors and the status data from the various subsystems, and the controller 101 can control the various subsystems in response to the input data 111. The controller can provide instructions to the various subsystems. The various subsystems of the CETEES act on the patient 110 and provide data regarding subsystem status and/or patient status, and the various meters, also referred to as sensors, of the CETEES can collect data from the patient 110. The ventilation subsystem 104, the electrode contact force enhancing subsystem 107, the forced exhalation subsystem, including the muscle stimulation subsystem 109, and the circumferential constriction subsystem 108 can act on the thorax of the patient. The countershock subsystem 102 and the acoustical or vibratory energy subsystem 103 can act on the myocardium 305 of the patient. The vagus nerve stimulation subsystem 105 can act on the vagus nerve of the patient.

Details of Subsystems

The ventilation subsystem 104 can include a ventilator that provides air to and/or controls the breathing of a sedated patient 110. The controller 101 can coordinate and synchronize the ventilation subsystem 104 and the countershock subsystem 102. The controller can provide instructions to the ventilation subsystem 104 and to the countershock subsystem 102, so that the countershock subsystem 102 can deliver a shock to the patient at the end of expiration when the patient's lungs are at or near maximum exhalation.

The forced exhalation subsystem(s) can include multiple separate subsystems. The force exhalation subsystem(s) can include one or more pneumatic bladders, one or more mechanical actuators, muscle electrical stimulators, and/or one or more constriction belts, or other means for squeezing the air out of a patient and minimizing lung volume. This can include the circumferential constriction subsystem, various pneumatic bladders, non-distensible belts, or various other means for constricting or squeezing the thorax of the patient 110 and/or muscle stimulators that can cause the patient to exhale. The controller can coordinate and synchronize the forced exhalation subsystem(s) and the countershock subsystem 102. The controller can provide instructions to the forced exhalation subsystem(s) and to the countershock subsystem 102, so that the countershock subsystem 102 can deliver a shock to the patient at the end of expiration when the patient's lungs are at or near a minimum volume. As a non-limiting example, a controller can coordinate and synchronize the timing of the forced exhalation subsystem and the countershock subsystem so that the forced exhalation subsystem can start to force exhalation at least from approximately 20% of the respiratory cycle length before electrical discharge through completion of electrical discharge. This allows adequate time for movement of the anatomic chest structures. Alteration of thoracic and lung anatomy so as to achieve minimized lung and transthoracic volumes may requires 2 to 3 seconds to be achieved.

The muscle stimulation subsystem 109 can include one or more cutaneous electrodes for muscle stimulation to force the sedated patient to exhale. The muscle stimulation subsystem 109 can include transcutaneous functional electrical stimulation (FES) that can cause one or more respiratory muscles to contract, as described in U.S. Patent Application Publication No. 2002/0128686 titled ABDOMINAL BELT WITH ADJUSTABLE ELECTRODES, the entire disclosure of which is incorporated herein by reference. FES of the rectus abdominus can act to assist exhalation by triggering the muscles of the patient to force air out of the patient's lungs. The controller can coordinate and synchronize the muscle stimulation subsystem 109 and the countershock subsystem 102. The controller can provide instructions to the muscle stimulation subsystem 109 and to the countershock subsystem 102, so that the countershock subsystem 102 can deliver a shock to the patient when the patient has exhaled.

The acoustical or vibratory energy subsystem 103 can apply acoustical and/or vibratory energy to the heart. The controller can coordinate and synchronize the acoustical or vibratory energy subsystem 103 and the countershock subsystem 102. The controller can provide instructions to the acoustical or vibratory energy subsystem 103 and to the countershock subsystem 102, so that controller can coordinate the timing when the countershock subsystem 102 delivers a shock to the patient and when the acoustical or vibratory energy subsystem 103 delivers energy to the heart. In some cases, the longest possible period of application of acoustical or vibratory energy may enhance the adjunctive effect. The acoustical or vibratory energy may affect the myocardium on a timeframe of seconds to minutes. In various embodiments, the acoustic, ultrasound or vibratory energy might initiate a number of seconds before electrical discharge and end coincident with termination of electrical discharge. In various embodiments, the acoustical or vibratory energy might be transmitted continuously during pacing or coincident with each electrical discharge.

The vagal nerve stimulator 105 can stimulate the vagus nerve of the patient. The controller can coordinate and synchronize the vagal nerve stimulator subsystem 105 and the countershock subsystem 102. The controller can provide instructions to the vagal nerve stimulation subsystem 105 and to the countershock subsystem 102, so that controller can coordinate the timing when the countershock subsystem 102 delivers a shock to the patient and when the vagal nerve stimulation subsystem 105 provides stimulation to the vagal nerve. Vagal nerve stimulation may affect the myocardium on a timeframe of tens of minutes. In some cases, the longest possible period of application may enhance the effect. In various embodiments, the vagal nerve stimulator might initiate a number of seconds or minutes before electrical discharge and end coincident with termination of electrical discharge. In various embodiments, the vagus nerve stimulator subsystem might transmit continuously during pacing or coincident with each electrical discharge.

The various subsystems of the CETEES that interact with the patient, including the ventilation subsystem 104, the electrode contact force enhancing subsystem 107, the forced exhalation subsystem(s), the muscle stimulation subsystem 109, the acoustical or vibratory energy subsystem 103, and/or the vagus nerve stimulation subsystem 105 can be optimized and synchronized with the countershock subsystem 102 so as the improve the efficacy of countershock. The various subsystems can be optimized and synchronized by the processor 101. The control system may use pre-defined a priori sequences and parameter values, and/or may optimize all components in response to biomarker or subsystem status feedback, as explained above.

The CETEES can adjunctively enhance the efficacy of electrical countershock or pacing by means of enhancing current flow and/or altering the myocardial substrate. Depending on the specific adjunctive subsystem or subsystems, the temporal relationships, more specifically the synchronizations, between current flow and the activation of the other subsystems may be different. Furthermore, the synchronization of each different subsystem can be optimized individually for each patent.

In various embodiments, a CETEES can have many or all of the various components and subsystems preinstalled within an inelastic outer shell capable of being placed circumferentially around the thorax at the level of the myocardium 305. This shell may be made of various fabric materials and incorporate a closure mechanism allowing appropriate sizing. This shell allows subsystems applying mechanical, acoustical, and electrical forces to have mechanical structure to maintain optimal configuration and apply Newtonian counterforce against. The shell also allows doctors and/or medical providers to operate with improved efficiency as all of the incorporated components can be applied to the patient quickly at one time instead of applying each component to the patient separately.

The patient-facing components for electrical countershock, such as adhesive gel electrodes, and the associated electronics such as the processor may be fully incorporated into the housing of an automated mechanical/pneumatic CETEES system. In various embodiments, one or more components of the electrical countershock subsystem can be housed separately from the main device. In the case of the countershock subsystem, it can be housed separately and connected to the main device by electrical cables. A system integrating multiple adjunctive enhancements with cardioversion or pacing can, at any given moment, only be applying a subset of its multiple modalities.

Figure 8:
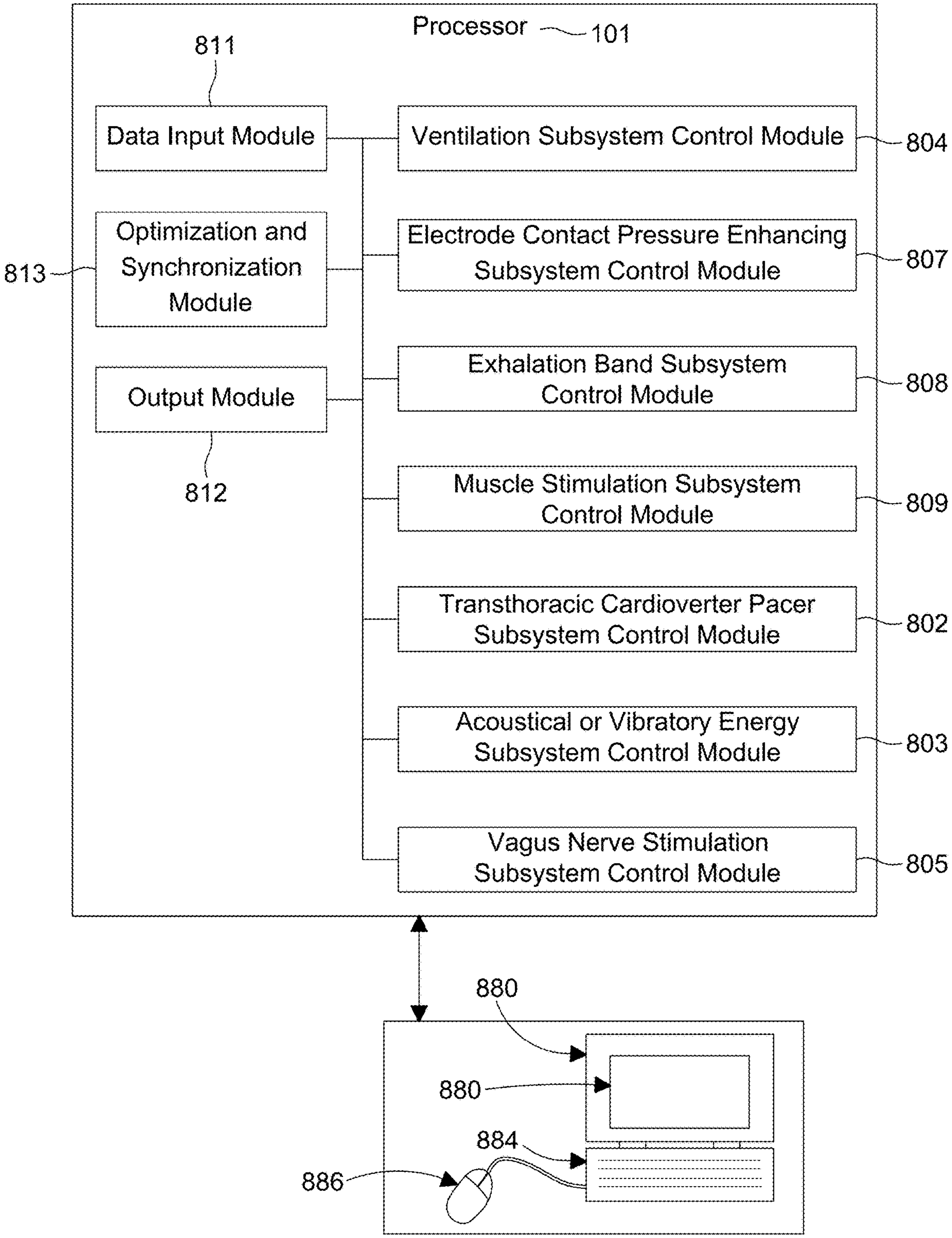
FIG. 8 is an overview of a processing and controlling system for a CETEES, according to an illustrative embodiment.

FIG. 8 is an overview of a processing and controlling system for a CETEES, according to an illustrative embodiment. A CETEES can be controlled by a controller, also called a processor, 101 that can include a plurality of modules, data inputs, and control outputs, and a user interface. The processor can be contained within a general purpose, or a dedicated, computing device 860, such as a PC, laptop, tablet, or smartphone. In various embodiments, the computing device 860 can be built into, or incorporated within, the housing of the CETEES. The computing device can include a user interface that can be a keyboard 864, mouse 866, touch screen or similar device, and a display 862 that can include a graphic user interface screen. In practice, a user can input instructions for a procedure through the user interface 864 into the processor 101. The modules and/or sub-modules can then process the instructions, collect measurements, and provide information to the various subsystems of the CETEES.

The processor unit 101 can include a data input module 811 and an optimization and synchronization module 813 that can be used by the processor to optimize the performance of the CETEES. The data input module 811 can input data 111 collected from various meters, also referred to as afferent limbs, and the data input module 811 can input data 111 collected from various subsystems, also referred to as effector limbs. The optimization and synchronization module can use the collected data to optimize and synchronize the various subsystems. The optimization and synchronization module 813 can optimize various subsystems by, for example, monitoring subsystem operating parameters as the parameters are adjusted and monitoring biomarker data as the parameters are adjusted to identify the parameter values at the onset of biomarker plateaus, as explained above, so that those parameter values can be used in the optimization of treatment. The optimization and synchronization module 813 can also apply machine learning to the various data to create patient specific algorithms for identifying which biomarkers and/or what biomarker values can be used to most effectively increase treatment efficacy. In various embodiments, the processor unit 101 can start with predetermined parameter values most likely to lead to the best treatment efficacy, and the optimization and synchronization module 813 can optimize various parameter values in real-time in response to data collected by the data input module 811. The control system can begin treatment with predetermined parameter values, and then the optimization and synchronization module 813 can optimize in real time to improve treatment as the treatment is occurring by collecting biomarker measurements and adjusting various subsystems in response to the collected data. The control subsystem can also execute precision adaptive sequences targeted toward pre-determined optima. The output module 812 can provide outputs 112 to the various subsystems including instructions and parameters determined by the optimization and synchronization module 813.

The processor unit 101 can include a ventilation subsystem control module 804 that can control the functions of the ventilation subsystem. The processor unit 101 can include an electrode contact pressure enhancing subsystem control module 807 that can control the functions of the electrode contact pressure enhancing subsystem. The processor unit 101 can include an exhalation band subsystem control module 808 that can control the functions of the forced exhalation subsystem. The processor unit 101 can include a muscle stimulation subsystem control module 809 that can control the functions of the muscle stimulation subsystem. The processor unit 101 can include a countershock subsystem control module 802 that can control the functions of the countershock subsystem. The processor unit 101 can include an acoustical or vibratory energy subsystem control module 803 that can control the functions of the acoustical or vibratory energy subsystem. The processor unit 101 can include a vagus nerve stimulation subsystem control module 805 that can control the functions of the vagus nerve stimulation subsystem. The processor unit 101 can include a bus 820.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. The CETEES may incorporate any type of countershock electrode upon or within the patient. The CETEES may incorporate any pattern of electrodes upon or within the patient. The CETEES may incorporate any type of control system for the subsystems, including but not limited to: electronic circuits, electronic controllers, or computers. The CETEES may incorporate any one of a multiplicity of sensors for adaptive modification of the subsystems. Accordingly, this description is meant to be taken only by way of example, and not to otherwise limit the scope of this invention. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub— processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Accordingly, this description is meant to be taken only by way of example, and not to otherwise limit the scope of this invention.

Most electromechanical medical devices have control modules that may be similar to a modern digital computer, or may be operator based. Afferent limbs may be subsystems that provide measurements to the control module. Afferent limbs can also be referred to as afferent subsystems. Afferent limbs inputting to the control module may include measurements of clinically relevant biomarkers such as ECG, cardiovascular photoplethysmography, measure of ventilatory status, and others. Effector limbs may be those subsystems that affect the status of the patient in some manner. Effector limbs may also be referred to as effector subsystems. The overall system may be a closed loop in which the effect of the effector subsystems is measured by the afferent limb and the control module subsequently adjusts the effector subsystems.

The sequence, forces, and electrical properties of the subsystems can be computer controlled. The control system may use pre-defined a priori sequences and/or may optimize all components based on biomarker or subsystem status feedback. As used herein, "a priori" refers to parameters, conditions, timing, sequences, force levels, energy levels, etc. that have been previously determined to be effective, and can be pre-programed into the device so that they can be applied by the device immediately and automatically at the beginning of treatment. As used herein, "optimization" refers to the process of improving parameters in an iterative process that works towards ideal parameters. Optimization can mean iteratively adjusting and updating various parameters in response to biomarkers or other data collected from sensors that can be part of afferent limbs and/or effector limbs, explained more fully below.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention.

BIBLIOGRAPHY SECTION

Kirchhof P, Eckardt L, Loh P, et al. Anterior-posterior versus anterior-lateral electrode positions for external cardioversion of atrial fibrillation: a randomised trial. Lancet 2002;360(9342):1275-9. DOI: 10.1016/s0140-6736(02)11315-8.

Kerber R E, Grayzel J, Hoyt R, Marcus M, Kennedy J. Transthoracic resistance in human defibrillation. Influence of body weight, chest size, serial shocks, paddle size and paddle contact pressure. Circulation 1981;63(3):676-82. DOI: 10.1161/01.cir.63.3.676.

Ewy G A, Hellman D A, McClung S, Taren D. Influence of ventilation phase on transthoracic impedance and defibrillation effectiveness. Crit Care Med 1980;8:164-166.

Towe B C, Rho R. Ultrasonic cardiac pacing in the porcine model. IEEE Trans Biomed Eng 2006;53(7):1446-8. DOI: 10.1109/TBME.2006.875715.

Yap J Y Y, Keatch C, Lambert E, Woods W, Stoddart P R, Kameneva T. Critical Review of Transcutaneous Vagus Nerve Stimulation: Challenges for Translation to Clinical Practice. Front Neurosci 2020;14:284. DOI: 10.3389/fnins.2020.00284.

Zeemering S, Lankveld T A R, Bonizzi P, et al. The electrocardiogram as a predictor of successful pharmacological cardioversion and progression of atrial fibrillation. Europace 2018;20(7):e96-e104. DOI: 10.1093/europace/eux234.

Deakin C D, McLaren R M, Petley G W, Clewlow F, Dalrymple-Hay M J. Effects of positive end-expiratory pressure on transthoracic impedance—implications for defibrillation. Resuscitation 1998;37(1):9-12.

Ramirez F D, Fiset S L, Cleland M J, et al. Effect of Applying Force to Self-Adhesive Electrodes on Transthoracic Impedance: Implications for Electrical

What is claimed is:

The invention claimed is:

1. A Cardiac Electrical Therapy Efficacy Enhancement System (CETEES) to improve the efficacy of acute electrical therapies for patients suffering cardiac dysrhythmias with retained hemodynamics, the CETEES comprising:

a Transthoracic Cardioverter Pacer (TCP);

an electrode contact force enhancers adapted to press on a TCP electrode;

a controller that synchronizes the TCP and the electrode contact force enhancer so that the TCP administers an electrical discharge in synchrony with the application of force to the TCP electrode by the electrode contact force enhancer; and an inelastic outer shell adapted to contain and maintain the location of the electrode contact force enhancers and provide a Newtonian counterforce that allows the electrode contact force enhancer to apply inward force towards the center of the CETEES.

2. The CETEES of claim 1 further comprising a ventilator, wherein the controller synchronizes the ventilator with the TCP, so that the TCP delivers a shock when the ventilator is within twenty percent of its minimum exhalation volume.

3. The CETEES of claim 1 further comprising an exhalation band adapted to squeeze air out of a pulmonary system of a patient, wherein the controller synchronizes the exhalation band with the TCP so that the TCP delivers a shock when the exhalation band is within twenty percent of maximal exhalation.

4. The CETEES of claim 1 further comprising a transcutaneous vibratory energy emitter, wherein the controller synchronizes the vibratory energy emitter with the TCP.

5. The CETEES of claim 1 further comprising a transthoracic vagus nerve electromagnetic energy emitter adapted to stimulate a vagus nerve of a patient with electromagnetic energy, wherein the controller synchronizes the vagus nerve electromagnetic energy emitter with the TCP.

6. The CETEES of claim 1 further comprising a transcutaneous abdominal muscle electrical stimulator adapted to stimulate an abdominus rectus muscle to trigger exhalation, wherein the controller synchronizes the abdominal muscle electrical stimulator with the TCP.

7. The CETEES of claim 1 further comprising at least one biomarker sensor, wherein a force of compression applied by the electrode contact force enhancer is dependent on data from the at least one biomarker sensor.

8. The CETEES of claim 1 further comprising at least one impedance sensor adapted to collect impedance data from the patient, wherein a force of compression applied by the electrode contact force enhancer is dependent on data from the at least one impedance sensor, wherein the controller increases the force of compression to reduce impedance until a plateau develops in the data collected from the impedance sensor, and then the controller reduces the force of compression to a level of force that was applied at the onset of the plateau in the impedance data, and the controller synchronizes the contact force enhancer and the TCP so that the TCP delivers a shock when the contract force enhancer is applying the level of force that was applied at the onset of the plateau in the impedance data.

9. The CETEES of claim 1 further comprising at least two pairs of TCP electrodes, and wherein the controller controls the TCP to provide shocks through multiple sequential current paths across the chest.

10. A Cardiac Electrical Therapy Efficacy Enhancement System (CETEES) to improve the efficacy of acute electrical therapies for patients suffering cardiac dysrhythmias with retained hemodynamics, the CETEES comprising:

a Transthoracic Cardioverter Pacer (TCP);

an electrode contact force enhancers adapted to press on a TCP electrode;

a controller that synchronizes the TCP and the electrode contact force enhancer so that the TCP administers an electrical discharge in synchrony with the application of force to the TCP electrode by the electrode contact force enhancer; and a transcutaneous vibratory energy emitter, wherein the controller synchronizes the vibratory energy emitter with the TCP.

11. The CETEES of claim 10, further comprising an inelastic outer shell adapted to contain and maintain the location of the electrode contact force enhancers and provide a Newtonian counterforce that allows the electrode contact force enhancer to apply inward force towards the center of the CETEES.

12. The CETEES of claim 10, further comprising a ventilator, wherein the controller synchronizes the ventilator with the TCP, so that the TCP delivers a shock when the ventilator is within twenty percent of its minimum exhalation volume.

13. The CETEES of claim 10, further comprising an exhalation band adapted to squeeze air out of a pulmonary system of a patient, wherein the controller synchronizes the exhalation band with the TCP so that the TCP delivers a shock when the exhalation band is within twenty percent of maximal exhalation.

14. The CETEES of claim 10, further comprising a transthoracic vagus nerve electromagnetic energy emitter adapted to stimulate a vagus nerve of a patient with electromagnetic energy, wherein the controller synchronizes the vagus nerve electromagnetic energy emitter with the TCP.

15. The CETEES of claim 10, further comprising a transcutaneous abdominal muscle electrical stimulator adapted to stimulate an abdominus rectus muscle to trigger exhalation, wherein the controller synchronizes the abdominal muscle electrical stimulator with the TCP.

16. A Cardiac Electrical Therapy Efficacy Enhancement System (CETEES) to improve the efficacy of acute electrical therapies for patients suffering cardiac dysrhythmias with retained hemodynamics, the CETEES comprising:

a Transthoracic Cardioverter Pacer (TCP);

an electrode contact force enhancers adapted to press on a TCP electrode;

a controller that synchronizes the TCP and the electrode contact force enhancer so that the TCP administers an electrical discharge in synchrony with the application of force to the TCP electrode by the electrode contact force enhancer; and a transthoracic vagus nerve electromagnetic energy emitter adapted to stimulate a vagus nerve of a patient with electromagnetic energy, wherein the controller synchronizes the vagus nerve electromagnetic energy emitter with the TCP.

17. The CETEES of claim 16, further comprising an inelastic outer shell adapted to contain and maintain the location of the electrode contact force enhancers and provide a Newtonian counterforce that allows the electrode contact force enhancer to apply inward force towards the center of the CETEES.

18. The CETEES of claim 16, further comprising a ventilator, wherein the controller synchronizes the ventilator with the TCP, so that the TCP delivers a shock when the ventilator is within twenty percent of its minimum exhalation volume.

19. The CETEES of claim 16, further comprising an exhalation band adapted to squeeze air out of a pulmonary system of a patient, wherein the controller synchronizes the exhalation band with the TCP so that the TCP delivers a shock when the exhalation band is within twenty percent of maximal exhalation.

20. The CETEES of claim 16, further comprising a transcutaneous vibratory energy emitter, wherein the controller synchronizes the vibratory energy emitter with the TCP.

* * * * *